United States Patent
Haimanti et al.

(10) Patent No.: US 6,828,095 B1
(45) Date of Patent: Dec. 7, 2004

(54) MODULATORS OF MORPHOGEN EXPRESSION AND METHODS OF IDENTIFYING THE SAME

(75) Inventors: Dorai Haimanti, Lexington, MA (US); Herman Oppermann, Medway, MA (US); Kuber T. Sampath, Holliston, MA (US); Alyssa A. Shepard, Shrewsbury, MA (US)

(73) Assignee: Curis, Inc., Cambridge, MA (US)

( * ) Notice: Subject to any disclaimer, the term of this patent is extended or adjusted under 35 U.S.C. 154(b) by 0 days.

(21) Appl. No.: 09/423,821

(22) PCT Filed: May 28, 1998

(86) PCT No.: PCT/US98/11025

§ 371 (c)(1),
(2), (4) Date: May 15, 2001

(87) PCT Pub. No.: WO98/54344

PCT Pub. Date: Dec. 3, 1998

Related U.S. Application Data

(60) Provisional application No. 60/047,911, filed on May 29, 1997.

(51) Int. Cl.$^7$ .......................... C12Q 1/68; C12N 5/00; C12N 15/00; C07H 21/00
(52) U.S. Cl. ...................... 435/6; 435/69.1; 435/320.1; 435/325; 536/23.1
(58) Field of Search ............................. 435/69.1, 325, 435/320.1, 6; 536/23.1, 24.1

(56) References Cited

U.S. PATENT DOCUMENTS 5,643,720 A * 7/1997 Pfahl et al. .................... 435/6

FOREIGN PATENT DOCUMENTS

| WO | WO 95/33831 | 12/1995 |
| WO | WO 96/38590 | 12/1996 |

OTHER PUBLICATIONS

Pedersen et al. The biology of eukaryotic promoter prediction—a review. Computers and Chemistry 23 (1999) 191–207.*
Zanninni et al. Pax-8, a Paired Domain–Containing Protein, Binds to a Sequence Overlapping the Recognition Site of a homeodomain and Activates Transcription from Two Thyroid–Specific Promoters. Molecular and Cellular Biology, vol. 12/9:4230–4241, 1992.*
Dudley et al., "A requirement for bone morphogenic protein–7 during development of the mammalian kidney and eye", *Genes and Develop.* 9:2795–807 (1995).
Epstein et al., "Identification of a Pax paired domain recognition sequence and evidence for DNA–dependent conformation change", *J. Biol. Chem.* 269(11): 8355–8361 (1994).
Feng et al., "Structure and sequence of mouse bone morphogenetic protein–2 gene: comparison of the structures and promoter regions of BMP–2 and BMP–4 genes", *BBA 1218*: 221–224 (1994).
Feng et al., "The mouse bone morphogenetic protein–4 gene", J. Biol. Chem 270: 28364–73 (1995).
Ghosh–Choudhury et al., "Immortalized murine osteoblasts derived from mouse BMP–2–T–antigen expressing transgenic mice", *Endocrinology 137*: 331–39 (1996).
Gottesfeld et al., "Regulation of gene expression by small molecules", *Nature 387*: 202–5 (1997).
Hahn et al., "A bone morphogenetic protein subfamily: chromosomal localization of human genes for BMP–5, BMP–6 and BMP–7", *Genomics 14*: 759–62 (1992).
Ishibashi et al., "Expression of bone morphogenetic protein–7 mRNA in MDCK cells", *BBRC 193*: 235–39 (1993).
Luo et al., "BMP–7 is an inducer of nephrogenesis and is also required for eye development and skeletal patterning", *Genes and Develop.* 9: 2808–820 (1995).
Marker et al., "Chromosomal localization, embryonic expression and imprinting tests for BMP–7 on distal mouse chromosome 2", *Genomics 28*: 576–80 (1995).
Mundlos et al., "Heritable diseases of the skeleton. Part I: Molecular insights into skeletal development transcription factors and signaling pathways", *Faseb J.* 11(2): 125–132 (1997).
Ozakynak et al., "Osteogenic protein–1 mRNA in the uterine endometrium", *BBRC 234*: 242–46 (1997).
Ozkaynak et al., "Osteogenic protein–2", *J. Biol. Chem.* 267: 25220–227 (1992).
Sakaue et al., "Molecular cloning and characterization of human bone morphogenetic protein–5 gene promoter", *BBRC 221*: 768–772 (1996).
Wijngaard et al., "Genomic organization of the human bone morphogenetic protein–4 gene: molecular basis of multiple transcripts", *BBRC 219*: 789–94 (1996).

* cited by examiner

*Primary Examiner*—Elizabeth Kemmerer
*Assistant Examiner*—Regina M. DeBerry
(74) *Attorney, Agent, or Firm*—Ropes & Gray LLP

(57) ABSTRACT

Disclosed are methods and compositions for identifying compounds having an ability to modulate expression of a morphogen, particularly OP-1, OP-1 homologues and closely related proteins, using one or more OP-1-specific, non-coding sequences and a suitable reporter gene. In preferred embodiments, the OP-1-specific non-coding DNA sequence comprises a Pax-responsive OP-1-modulating element.

12 Claims, 3 Drawing Sheets

MODULATORS OF MORPHOGEN EXPRESSION AND METHODS OF IDENTIFYING THE SAME

This application claims the benefit of Provisional application Ser. No. 60/047,911, filed May 29, 1997.

FIELD OF THE INVENTION

The invention relates generally to the field of drug screening assays. More particularly, the invention relates to methods and compositions for identifying molecules that modulate expression of true tissue morphogenic proteins.

BACKGROUND OF THE INVENTION

A class of proteins recently has been identified, the members of which are true tissue morphogenic proteins. The members of this class of proteins are characterized as competent for inducing the developmental cascade of cellular and molecular events that culminate in the formation of new organ-specific tissue, including any vascular and connective tissue formation, as required by the naturally occurring tissue. Specifically, the morphogens are competent for inducing all of the following biological functions in a morphogenically permissive environment: (1) stimulating proliferation of progenitor cells; (2) stimulating differentiation of progenitor cells; (3) stimulating the proliferation of differentiated cells and (4) supporting the growth and maintenance of differentiated cells. For example, the morphogenic proteins can induce the full developmental cascade of bone tissue morphogenesis, including the migration and proliferation of mesenchymal cells, proliferation and differentiation of chondrocytes, cartilage matrix formation and calcification, vascular invasion, osteoblast proliferation, bone formation, bone remodeling, and hematopoietic bone marrow differentiation. These proteins also have been shown to induce true tissue morphogenesis of non-chondrogenic tissue, including dentin, liver, and nerve tissue.

A particularly useful tissue morphogenic protein is human OP-1 (Osteogenic Protein-1), described in U.S. Pat. No. 5,011,691; U.S. Pat. No. 5,266,683 and Ozkaynak et al. (1990) *EMBO J.* 9: 2085–2093. Species homologues identified to date include, but are not limited to, mouse OP-1 (see U.S. Pat. No. 5,266,683) and the Drosophila homologue 60A, described in Wharton et al. (1991) *Proc. Nat. Acad. Sci. USA* 88:9214–9218). Other closely related proteins include OP-2 (Ozkaynak (1992) *J. Biol. Chem.* 2:25220–25227 and U.S. Pat. No. 5,266,683); BMP5, BMP6 (Celeste et al. (1991) *Proc. Natl. Acad. Sci.* 8:9843–9847) and Vgr-1 (Lyons et al. (1989). These disclosures are incorporated herein by reference.

It previously has been contemplated that these tissue morphogens can be administered to an animal to regenerate lost or damaged tissue. Certain complications, however, presently are encountered during the production, formulation and use in vivo of therapeutic macromolecules, such as morphogen proteins. For example, such proteins are typically produced by fermentation or culture of suitable host cells. Any biological product produced from such host cells for use in humans presently must be shown to be essentially free of host cell contaminants, such as secreted or shed proteins, viral particles or degradation products thereof. Providing such assurance can add significantly to the cost and technical difficulty of commercial production of biological macromolecules. Furthermore, appropriate formulations must be developed for conferring commercially reasonable shelf life on the produced macromolecule, without significant loss of biological efficacy. An additional complicating factor arises when circumstances warrant an extended course of therapeutic treatment with the produced and formulated macromolecule: the treated mammal may develop an immunological response to the macromolecule, and any such response may interfere with effectiveness thereof. In extreme circumstances, treatment must be discontinued.

Alternatively, administering a molecule capable of modulating expression of the endogenous tissue morphogen is an effective means for providing morphogen to a site in vivo. For example, DNA sequences have been identified in the OP-1 gene promoter that resemble wt-1/Egr-1 consensus sequences, TLC binding sequences, FTZ binding sequences and steroid binding sequences (see WO 95/33831, the disclosure of which is incorporated herein by reference). Thus, molecules to which these regulatory sequences are responsive are likely modulators of the OP-1 gene and can influence its expression.

It is an object of this invention to provide compositions and methods of identifying compounds which can modulate expression of an endogenous tissue morphogen, particularly OP-1 and other members of the larger genus of true tissue morphogens. The compounds thus identified have utility both in vitro and in vivo. Useful compounds contemplated include at least those that are capable of stimulating transcription and/or translation of the OP-1 gene, as well as compounds capable of inhibiting transcription and/or translation of the OP-1 gene, via OP-1 non-coding DNA sequences resembling consensus sequences for Pax homeobox genes, in particular, the Pax 6 or Pax 2 genes.

These and other objects and features of the invention will be apparent from the description, drawings and claims which follow.

SUMMARY OF THE INVENTION

The invention features compositions and methods for screening candidate compounds for their ability to modulate the effective local or systemic levels of endogenous morphogen, particularly OP-1, in an organism. In one aspect, the method is practiced by: (I) incubating one or more candidate compounds with cells transfected with a DNA sequence encoding at least a portion of a morphogen non-coding DNA sequence that is responsive to a Pax homeobox gene and which is competent to act on and affect expression of a reporter gene with which it is operatively associated; (2) measuring the level of reporter gene expression in the transfected cell, and (3) comparing the level of reporter gene expressed in the presence of the candidate compound with the level of reporter gene expressed in the absence of the candidate compound. The level of an expressed reporter gene product in a given cell culture, or a change in that level resulting from exposure to one or more compound(s) indicates that the compound can also modulate the level of the morphogen normally associated with the non-coding sequence. Specifically, an increase in the level of reporter gene expression is indicative of a candidate compound's ability also to increase morphogen expression in vivo. Similarly, a decrease in the level of reporter gene expression is indicative of a candidate compound's ability also to decrease or otherwise interfere with morphogen expression in vivo. The above method is particularly useful for identifying compounds that are capable of influencing Pax mediated OP-1 gene expression.

The methods of the invention can therefore be used to identify compounds showing promise as therapeutics for various in vivo and ex vivo mammalian applications, as well as to identify compounds having numerous utilities. For example, compounds that modulate morphogen expression by stimulating Pax 2 or Pax 6 mediated transcription of a morphogen can be used in vivo to correct or alleviate a disease condition, to regenerate lost or damaged tissue, to induce cell proliferation and differentiation, and/or to maintain cell and tissue viability and/or a differentiated phenotype in vivo or ex vivo. The compounds also can be used to maintain the viability of, and the differentiated phenotype of, cells in culture. The various in vivo, ex vivo, and in vitro utilities and applications of the morphogenic proteins described herein are well documented in the art. See, for example, US 92/01968 (WO 94/03200), filed Mar. 11, 1992; US 92/07358 (WO 93/04692), filed August 28; PCT US 92/0743 (WO 93/05751), filed Aug. 28, 1992; US 93/07321 (WO 94/03200), filed Jul. 29, 1993; US 93/08808 (WO 94/06449), filed Sep. 16, 1993; US93/08885 (WO94/06420), filed Sep. 15, 1993, and U.S. Pat. No. 5,266,683.

In another aspect, the invention further provides vectors and cells useful for morphogen, particularly OP-1, therapy. In one embodiment, the invention features a vector having a reporter gene operatively associated with at least a portion of one or more OP-1 non-coding sequences responsive to Pax homeobox gene products. The OP-1 non-coding sequences comprise at least a first Pax responsive OP-1 modulating element which is responsive to a first Pax gene expression product. In other embodiments, vectors further comprise a second non-coding sequence comprising at least a second Pax-responsive OP-1 modulating element which is responsive to a second Pax gene expression product; in such embodiments, the first and second Pax gene expression product differ. OP-1 non-coding sequences which are Pax responsive OP-1 modulating elements can be selected from nucleotides 1–3317 of SEQ ID No. 1. Also anticipated to be similarly useful are certain of the non-coding sequences of other species homologues of OP-1 and proteins closely related to OP-1. For example, other non-coding DNA that is responsive to Pax gene products or homologues thereof can be used to identify modulators of specific morphogens, or other factors capable of modulating morphogen gene expression.

In another embodiment, the vector can include a non-coding OP-1-specific sequence selected from at least one of the following sequence segments of SEQ. ID No. 1 presented below, which defines approximately 3.3 Kb of 5' non-coding human genomic OP-1 sequence. Preferred vectors comprise sequence segments including nucleotides 1–3317, as well as shorter fragments of this region of DNA such as approximately nucleotides 108–121, 139–154, 157–167, 365–378, 491–503, 598–613, 737–747, 891–903, 994–1006, 1123–1140, 1144–1161, 1285–1297, 1750–1762, 2001–2023, 2365–2378, 2931–2944 of SEQ. ID No. 1, including allelic, species and other sequence variants thereof. As base 2790 is the mRNA start site, other preferred sequences include approximately 2790–3317, representing transcribed but not translated 5' non-coding sequence and shorter fragments of this DNA region. Other preferred regions of the 5' non-coding region of SEQ. ID No. 1 include regions comprising a cluster of several Pax responsive elements, such as, for example, approximately 1–2073, 1–1297, 1–2691, 1–378, 491–1006, 1750–2023, 1750–2378, 1750–2691, 1750–2944. In certain embodiments, non-coding sequences correspond to part or all of SEQ. ID No. 2 and/or SEQ. ID No. 3, including allelic, species and other sequence variants thereof. In yet other embodiments, vectors comprise non-coding sequences corresponding to at least one, preferably between one and twelve and/or four or more first and second Pax-responsive OP-1 modulating elements, respectively. First Pax-responsive sites correspond approximately to bases 108–121, 139–154, 157–167, 365–378, 497–511, 598–613, 1123–1140, 1144–1161, 1285–1297, 1750–1762, 2001–2023, 2365–2378 and 2931–2944 of SEQ. ID No. 1. Second Pax-responsive sites correspond approximately to bases 491–503, 737–747, 891–903, and 994–1006 of SEQ. ID No. 1.

In another aspect, the invention provides a cell comprising a reporter gene whose regulation is mediated by one or more of the Pax-responsive OP-1 non-coding sequences defined above. In one embodiment, the cell is transfected with a reporter gene in operative association with at least one Pax responsive site. In another embodiment, the present invention provides a cell comprising a transfected vector encoding a reporter gene operatively associated with at least two DNA sequences, the first comprising at least part of a sequence selected from SEQ. ID No. 2 while the second comprises at least part of a sequence selected from SEQ. ID No. 3, including allelic, species and other sequence variants of the foregoing. In yet another embodiment, cells of the present invention are co-transfected with expression vectors encoding Pax gene expression products such as, for example, Pax 2 and/or Pax 6.

In another aspect, the invention provides kits useful in the design and/or identification of OP-1 expression modulating compounds. As used herein a "kit" comprises a cell comprising a reporter gene in operative association with an OP-1 non-coding DNA sequence and the reagents necessary for detecting expression of the reporter gene. The portion of OP-1 noncoding DNA chosen can be any of the various sequences which have been described herein above.

Following this disclosure, medium flux screen assays, and kits therefore, for identifying modulators of morphogen expression, such as OP-1 expression, are available. These compounds can be naturally occurring molecules, or they can be designed and biosynthetically created using a rational drug design and an established structure/function analysis methodology. The compounds can be amino acid-based or can be composed in part or wholly of non-proteinaceous synthetic organic molecules.

The OP-1 expression modulating compounds thus identified can be produced in reasonable quantities, including commercially significant quantities, using standard recombinant expression or chemical synthesis technology well known and characterized in the art and/or as described herein. For example, automated means for the chemical synthesis of nucleic and amino acid sequences are commercially available. Alternatively, promising candidate compounds can be modified using standard biological or chemical methodologies to, for example, enhance the binding affinity of the compound for a DNA element and the preferred candidate compound derivative then can be produced in quantity.

Once a candidate compound has been identified and produced, it can be further tested for its effect on OP-1 expression. For example, a compound which upregulates (increases) the production of OP-1 (e.g., an OP-1 agonist) in a kidney cell line is a candidate for systemic administration. The candidate compound can be assayed in an animal model to determine the candidate molecule's efficacy in vivo. For example, the ability of a compound to upregulate levels of circulating OP-1 in vivo can be used to correct bone metabolism diseases such as osteoporosis (See, for example, PCT/US92/07932, above). Conversely, compounds which down regulate (decrease) the production of OP-1 (e.g., OP-1 antagonists) are also contemplated to be useful. Useful in vivo animal models for systemic administration are disclosed in the art and below.

As is well known in the art, OP-1 is differentially expressed in different cell types. Accordingly, it is further anticipated that a candidate compound will have utility as an inducer of OP-1 expression in one cell type but not in another. Thus, the invention further contemplates testing a candidate compound for its utility in modulating expression of OP-1 in a tissue specific manner in vivo.

Thus, in view of this disclosure, one of ordinary skill in recombinant DNA and tissue culture techniques can design and construct appropriate DNA vectors and transfect cells with appropriate DNA sequences for use in the method according to the invention to assay for compounds which modulate the expression of OP-1. These identified compounds can be used to modulate OP-1 production and its effective concentrations in both in vivo and in vitro.

DETAILED DESCRIPTION

Figures 1A, 1B:
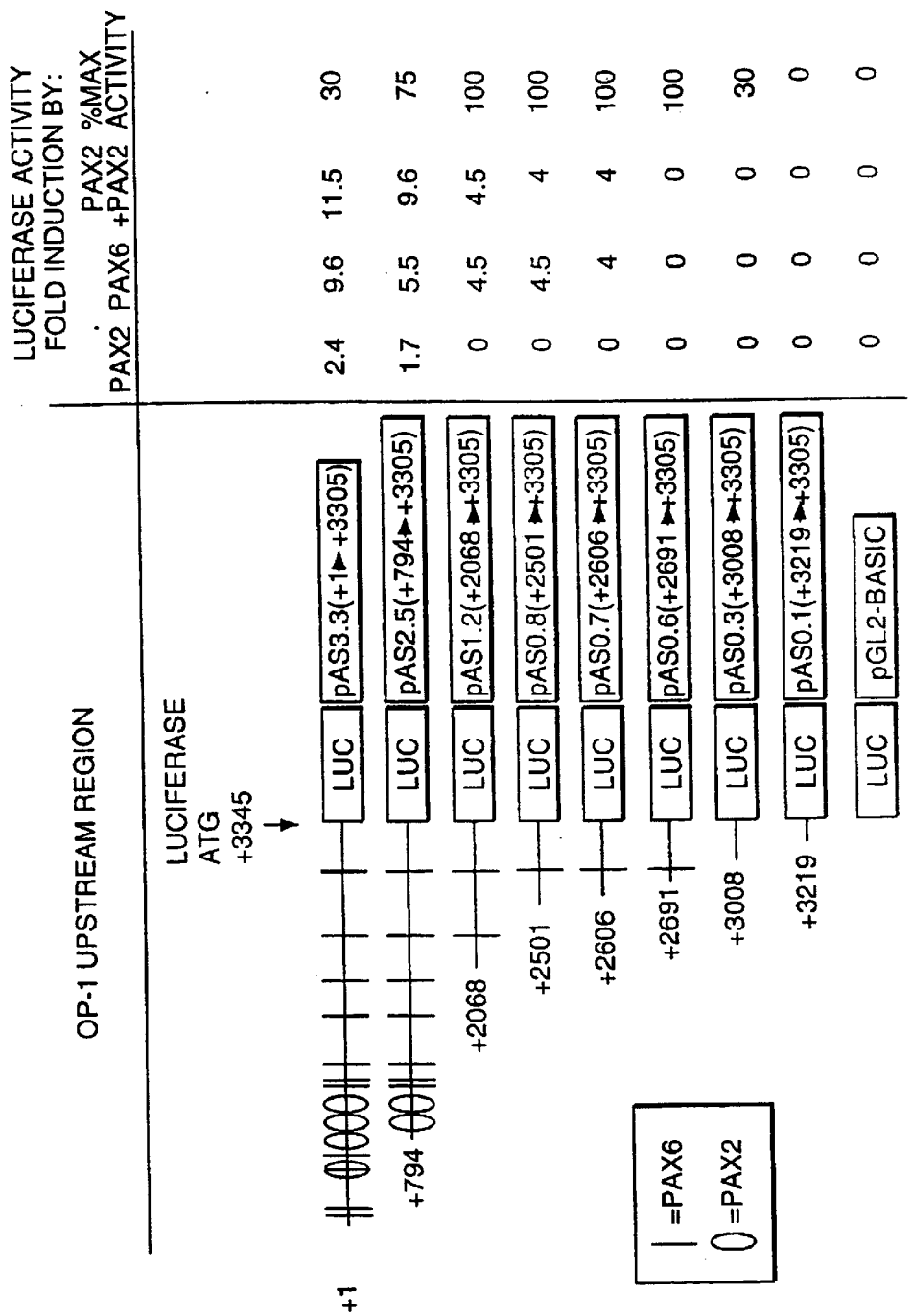
FIG. 1A is a diagrammatical illustration of the 5' non-coding region of the OP-1 gene in operative association with a luciferase reporter gene. Certain preferred Pax consensus sites are depicted along the non-coding region.
FIG. 1B is a graphical representation of the induction of luciferase activity in G401 human kidney cells transfected with OP-1 promoter deletion constructs of (1A) in the presence or absence of co-transfection with Pax 2 and/or Pax 6 expression constructs.

As will be more fully described below, we have discovered specific regions in the OP-1 gene sequence useful in identifying molecules capable of modulating OP-1 expression in vivo. We discovered DNA sequences responsible for the regulation of OP-1 gene expression by cloning and characterizing various truncated sequences isolated from the 5' non-coding sequences of the human OP-1 gene. The presence of sequences defining Pax 2 or Pax 6 consensus binding sequences as defined herein in the OP-1 non-coding region, together with the observed modulation of OP-1 gene expression mediated by Pax 2 and Pax 6 gene products, implicate these sequences, or variants thereof, as having utility in a method for the screening of compounds for their ability to modulate OP-1 expression. Moreover, Pax responsive sequences located in 5' non-coding sequences of other morphogen genes provide a means for identifying compounds that modulate expression of other such morphogens.

List of Useful Terms and Definitions

As used herein, "morphogen" means the class of proteins typified by human osteogenic protein 1 (hOP-1). hOP-1 and functionally equivalent morphogens are, as defined herein, dimeric proteins that induce or reinduce mammalian cells, particularly uncommitted progenitor cells, to undergo a fully integrated developmental cascade of cellular and molecular events that culminates in the formation of fully differentiated, functional tissue of a type appropriate to the context or local biological environment in which morphogenesis is induced, including any vascularization, connective tissue formation, enervation and the like characteristic of tissue naturally-occurring in such a context. For example, if cells are stimulated by OP-1 in the context of, for example, bone, liver, nerve, tooth dentin, periodontal tissue, gastrointestinal tract lining tissue, the resulting cascade of morphogenesis culminates in the formation of new or regenerative differentiated tissue appropriate to that local environment. Morphogenesis therefore differs significantly from simple reparative healing processes in which scar tissue (e.g., fibrous connective tissue) is formed and fills a lesion or other defect in differentiated, functional tissue.

Morphogens generally induce all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells. The term "progenitor cells" includes uncommitted cells, preferably of mammalian origin, that are competent to differentiate into one or more specific types of differentiated cells, depending on their genomic repertoire and the tissue specificity of the permissive environment in which morphogenesis is induced. Preferably, morphogenesis culminates in the formation of differentiated tissue having structural and functional properties of a tissue that occurs naturally in the body of a mammal. Morphogens further can delay or mitigate the onset of senescence- or quiescence-associated Loss of phenotype and/or tissue function. Morphogens still further can stimulate phenotypic expression of differentiated cells, including expression of metabolic and/or functional, e.g., secretory, properties thereof. In addition, morphogens can induce redifferentiation of transformed cells under appropriate environmental conditions. As noted above, morphogens that induce proliferation and differentiation at least of mammalian bone progenitor cells, and/or support the formation, growth, maintenance and functional properties of mammalian endochondral bone tissue, are representative.

A morphogen as isolated from natural sources in mature, biologically active form is a glycosylated dimer typically having an apparent molecular weight of about 30–36 kDa as determined by SDS-PAGE. When reduced, the 30 kDa protein gives rise to two glycosylated peptide subunits having apparent molecular weights of about 16 kDa and 18 kDa. The reduced polypeptides themselves have no detectable morphogenic activity. Glycosylation, however, is not required for biological activity. The unglycosylated protein has an apparent molecular weight of about 27 kDa. When reduced, the 27 kDa protein gives rise to two unglycosylated polypeptides having molecular weights of about 14 kDa to 16 kDa. The polypeptides which together form the biologically active dimer comprise at least six, preferably at least seven, positionally conserved cysteine residues as set forth in U.S. Ser. No. 08/396,930 now abandoned, the teachings of which have been incorporated herein by reference. As described above, particularly preferred sequences include those comprising the C-terminal 96 or 102 amino acid sequences of DPP (from Drosophila), Vg1 (from Xenopus), Vgr-1 (from mouse), the OP-1 and OP2 proteins, proteins (see U.S. Pat. No. 5,011,691 and Oppermann et al., as well as the proteins referred to as BMP2, BMP3, BMP4 (see WO88/00205, U.S. Pat. No. 5,013,649 and WO91/18098), BMP5 and BMP6 (see WO90/11366, PCT/US90/01630), BMP8 and BMP9.

As stated above, the representative morphogen, for purposes of the present invention, comprises an OP-1 or an OP-1-related polypeptide. Sequences of useful OP-1 polypeptides are recited in U.S. Pat. Nos. 5,011,691; 5,018,753 and 5,266,683; in Ozkaynak et al. (1990) *EMBO J.* 2:2085–2093; and Sampath et al. (1993) *Proc. Natl. Acad Sci. USA* 90:6004–6008. Additional useful sequences occur in the C-terminal domains of DPP (from Drosophila), Vg1 (from Xenopus), 60A (from Drosophila, see Wharton et al. (1991), *Proc. Natl. Acad. Sci. USA* 88:9214–9218), Vgr-1 (from mouse), the OP-1 and OP2 proteins, (see U.S. Pat. No. 5,011,691 by Oppermann et al.), as well as the proteins referred to as BMP2, BMP3, BMP4 (see WO88/00205, U.S. Pat. No. 5,013,649 and WO91/18098), BMP5 and BMP6 (see WO90/11366, PCT/US90/01630) and BMP8 and 9. Each of the foregoing polypeptides, when oxidized and dimerized, is useful as a morphogen herein. Further, this family of morphogenic proteins includes longer forms of a given protein, as well as phylogenetic, e.g., species and allelic variants and biosynthetic mutants thereof, including addition and deletion mutants and variants, such as those which may alter the conserved C-terminal cysteine skeleton, provided that the alteration still allows the protein to form a dimeric species having a conformation capable of inducing morphogenesis, e.g., endochondral bone formation when implanted in a mammal in conjunction with a matrix permissive of bone morphogenesis. In addition, morphogens as defined herein can include forms having varying glycosylation patterns and varying N-termini, can be naturally occurring or biosynthetically derived, and can be produced by expression of recombinant DNA in prokaryotic or eukaryotic host cells according to established techniques. The proteins are active either as homodimers or heterodimers.

As used herein, the terms "morphogen", "bone morphogen", "bone morphogenic protein", "BMP", "osteogenic protein" and "osteogenic factor" embrace the class of proteins a typified by human osteogenic protein 1 (hOP-1). It will be appreciated by the artisan of ordinary skill in the art, however, that OP-1 merely is representative of the TGF-β subclass of true tissue morphogens competent to act as osteogenic proteins, and is not intended to limit the description. Morphogenic protein is generally understood to mean a protein which can induce the full cascade of morphogenic events culminating in at least endochondral bone formation. Other known, and useful proteins include, OP2, OP3, BMP-2, BMP-3, BMP-3b, BMP-4, BMP-5, BMP-6, BMP-8, BMP-9, BMP-10, BMP-11, BMP-12, BMP-13, BMP-15, GDF-1, GDF-2, GDF-3, GDF-5, GDF-6, GDF-7, GDF-8, GDF-9, GDF-10, GDF-11, GDF-12, Vg1, Vgr, 60A, DPP, NODAL, UNIVIN, SCREW, ADMP, NEURAL and morphogenically active amino acid variants thereof. As defined herein, morphogenic proteins include biologically active species variants of any of these proteins, including conservative amino acid sequence variants, proteins encoded by degenerate nucleotide sequence variants, and morphogenically active proteins sharing the conserved seven cysteine skeleton as defined herein and encoded by a DNA sequence competent to hybridize to a DNA sequence encoding an osteogenic protein disclosed herein, including, without limitation, OP-1, BMP-5, BMP-6, BMP-2, BMP-4 or GDF-5, GDF-6 or GDF-7. Morphogenic proteins include those sharing the conserved seven cysteine domain and sharing at least 70% amino acid sequence homology (similarity) within the C-terminal active domain, as defined herein. That is, particularly preferred morphogenic proteins are those comprising an amino acid sequence having at least 70% homology with the C-terminal 102–106 amino acids, defining the conserved seven cysteine domain, of human OP-1 and related proteins. Certain preferred embodiments of the instant invention relate to the morphogenic protein, OP-1. "Amino acid sequence homology" is understood herein to mean amino acid sequence similarity. Homologous sequences share identical or similar amino acid residues, where similar residues are conservative substitutions for, or allowed point mutations of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. Examples of conservative variations include the substitution of one hydrophobic residue, such as isoleucine, valine, leucine or methionine, for another, or the substitution of one polar residue for another, such as the substitution of arginine for lysine, glutamic acid for aspartic acid, or glutamine for asparagine, and the like. The term "conservative variation" also includes the use of a substituted amino acid in place of an unsubstituted parent amino acid, provided that antibodies raised to the substituted polypeptide also immunoreact with the unsubstituted polypeptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; phenylalanine, and tyrosine.

Naturally occurring proteins identified and/or appreciated herein to be morphogenic proteins form a distinct subgroup within the loose evolutionary grouping of sequence-related proteins known as the TGF-β superfamily or supergene family. The naturally occurring morphogens share substantial amino acid sequence homology in their C-terminal regions (domains). Morphogenic proteins comprise a pair of polypeptides with amino acid sequences each comprising a sequence that shares a defined relationship with an amino acid sequence of a reference morphogen. Herein, preferred morphogenic polypeptides share a defined relationship with a sequence present in active human OP-1. However, any one or more of the naturally occurring or biosynthetic sequences disclosed herein similarly could be used as a reference sequence. Preferred osteogenic polypeptides share a defined relationship with at least the C-terminal six cysteine domain of human OP-1. Preferably, morphogenic polypeptides share a defined relationship with at least the C-terminal seven cysteine domain of human OP-1. That is, preferred polypeptides in a dimeric protein with morphogenic activity each comprise a sequence that corresponds to a reference sequence or is functionally equivalent thereto.

Functionally equivalent sequences include functionally equivalent arrangements of cysteine residues disposed within the reference sequence, including amino acid insertions or deletions which alter the linear arrangement of these cysteines, but do not materially impair their relationship in the folded structure of the dimeric morphogen protein, including their ability to form such intra- or inter-chain disulfide bonds as may be necessary for morphogenic activity. Functionally equivalent sequences further include those wherein one or more amino acid residues differs from the corresponding residue of a reference sequence, e.g., the C-terminal seven cysteine domain (also referred to herein as the conserved seven cysteine skeleton) of human OP-1, provided that this difference does not destroy morphogenic activity. Accordingly, conservative substitutions of corresponding amino acids in the reference sequence are preferred. Amino acid residues that are conservative substitutions for corresponding residues in a reference sequence are those that are physically or functionally similar to the corresponding reference residues, e.g., that have similar size, shape, electric charge, chemical properties including the ability to form covalent or hydrogen bonds, or the like. Particularly preferred conservative substitutions are those fulfilling the criteria defined for an accepted point mutation in Dayhoff et al. (1978), 5 *Atlas of Protein Sequence and Structure*, Suppl. 3, ch. 22 (p. 354–352), Natl. Biomed. Res. Found., Washington, D.C. 20007, the teachings of which are incorporated by reference herein.

Publications disclosing these sequences, as well as their chemical and physical properties, include: OP-1 and OP-2: U.S. Pat. No. 5,011,691, U.S. Pat. No. 5,266,683, Ozkaynak et al. (1990) *EMBO J.* 9: 2085–2093; OP-3: WO94110203 PCT US93/10520); BMP2, BMP3, BMP4: WO88/00265, Wozney et al. (1988) *Science* 242: 1528–1534); BMP5 and BMP6: Celeste et al (1991) *PNAS* 87: 9843–9847; Vgr-1: Lyons et al. (1989) *PNAS* 86: 4554–4558; DPP: Padgett et al. (1987) *Nature* 325: 81–84; Vg-1: Weeks (1987) *Cell* 51: 861–867; BMP-9: WO95/33830(PCT/US95/07084); BMP10: WO94/26893 (PCT/US94/05290); BMP-11: WO94/26892 (PCT/US94/05288); BMP12: WO95/16035 (PCT/US94/14030); BMP-13: WO95/16035 (PCT/US94/14030); GDF-1: WO92/00382 (PCT/US91/04096) and Lee et al. (1991) *PNAS* 88: 4250–4254; GDF-8: WO94/21681 (PCT/US94/03019); GDF-9: WO94/15966 (PCT/US94/00685); GDF-10: WO95/10539 (PCT/US94/11440); GDF-11: WO96/01845 (PCT/US95/08543); BMP-15: WO96/36710 (PCT/US96/06540); MP121: WO96/01316 (PCT/EP95/02552); GDF-5 (CDMP-1, MP52): WO94/15949 (PCT/US94/00657) and WO96/14335 (PCT/US94/12814) and WO93/16099 (PCT/EP93/00350); GDF (CDMP-2, BMP13): WO95/01801 (PCT/US94/07762) and WO96/14335 and WO95/10635 (PCT/US94/14030); GDF-7 (CDMP-3. BMP12): WO95/10802 (PCT/US94/07799) and WO95/10635 (PCT/US94/14030). In another embodiment, useful proteins include biologically active biosynthetic constructs, including novel biosynthetic morphogenic proteins and chimeric proteins designed using sequences from two or more known morphogens. See also the biosynthetic constructs disclosed in U.S. Pat. No. 5,011,691, the disclosure of which is incorporated herein by reference (e.g., COP-1, COP-3, COP-4, COP-5, COP-7, and COP-16).

As earlier stated, morphogenic proteins contemplated herein include those in which the amino acid sequences comprise a sequence sharing at least 70% amino acid sequence homology or "similarity", and preferably 80% homology or similarity, with a reference morphogenic protein selected from the foregoing naturally occurring proteins. Preferably, the reference protein is human OP-1, and the reference sequence thereof is the C-terminal seven cysteine domain present in osteogenically active forms of human OP-1. A polypeptide suspected of being functionally equivalent to a reference morphogen polypeptide is aligned therewith using the method of Needleman, et al. (1970) *J. Mol. Biol.* 48:443–453, implemented conveniently by computer programs such as the Align program (DNAstar, Inc.). As noted above, internal gaps and amino acid insertions in the candidate sequence are ignored for purposes of calculating the defined relationship, conventionally expressed as a level of amino acid sequence homology or identity, between the candidate and reference sequences. "Amino acid sequence homology" is understood herein to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence. In a currently preferred embodiment, the reference sequence is OP-1. Morphogenic proteins useful herein accordingly include allelic, phylogenetic counterpart and other variants of the preferred reference sequence, whether naturally-occurring or biosynthetically produced (e.g., including "muteins" or "mutant proteins"), as well as novel members of the general morphogenic family of proteins, including those set forth and identified above. Certain particularly preferred morphogenic polypeptides share at least 60% amino acid identity with the preferred reference sequence of human OP-1, still more preferably at least 65% amino acid identity therewith.

As noted above, certain currently preferred morphogenic polypeptide sequences have greater than 60% identity, preferably greater than 65% identity, with the amino acid sequence defining the preferred reference sequence of hOP-1. These particularly preferred sequences include allelic and phylogenetic counterpart variants of the OP-1 and OP-2 proteins, including the Drosophila 60A protein. Accordingly, preferred morphogenic proteins include active proteins comprising pairs of polypeptide chains within the generic amino acid sequence herein referred to as "OPX" (see below and SEQ ID NO: 4), which defines the seven cysteine skeleton. As described therein, each Xaa at a given position independently is selected from the residues occurring at the corresponding position in the C-terminal sequence of mouse or human OP-1 or OP-2.

```
Cys Xaa Xaa His Glu Leu Tyr Val Ser Phe Xaa Asp Leu Gly Trp Xaa Asp Trp
1            5                   10                 15

Xaa Ile Ala Pro Xaa Gly Tyr Xaa Ala Tyr Tyr Cys Glu Gly Glu Cys Xaa Phe Pro
         20              25              30                 35

Leu Xaa Ser Xaa Met Asn Ala Thr Asn His Ala Ile Xaa Gln Xaa Leu Val His Xaa
         40              45              50                 55

Xaa Xaa Pro Xaa Xaa Val Pro Lys Xaa Cys Cys Ala Pro Thr Xaa Leu Xaa Ala
             60              65              70

Xaa Ser Val Leu Tyr Xaa Asp Xaa Ser Xaa Asn Val Ile Leu Xaa Lys Xaa Arg
75              80              85                 90

Asn Met Val Val Xaa Ala Cys Gly Cys His
                95              100
``` wherein Xaa at res. 2=(Lys or Arg); Xaa at res. 3=(Lys or Arg); Xaa at res: 11=(Arg or Gln); Xaa at res. 16=(Gln or Leu); Xaa at res. 19=(Ile or Val); Xaa at res. 23=(Glu or Gln); Xaa at res. 26=(Ala or Ser); Xaa at res. 35=(Ala or Ser); Xaa at res. 39=(Asn or Asp); Xaa at res. 41=(Tyr or Cys); Xaa at res. 50=(Val or Leu); Xaa at res. 52=(Ser or Thr); Xaa at res. 56=(Phe or Leu); Xaa at res. 57=(Ile or Met); Xaa at res. 58=(Asn or Lys); Xaa at res. 60=(Glu, Asp or Asn); Xaa at res. 61=(Thr, Ala or Val); Xaa at res. 65=(Pro or Ala); Xaa at res. 71=(Gln or Lys); Xaa at res. 73=(Asn or Ser); Xaa at res. 75=(Ile or Thr); Xaa at res. 80=(Phe or Tyr); Xaa at res. 82=(Asp or Ser); Xaa at res. 84=(Ser or Asn); Xaa at res. 89=(Lys or Arg); Xaa at res. 91=(Tyr or His); and Xaa at res. 97=(Arg or Lys).

In yet other preferred embodiments, morphogenic protein as contemplated herein can be further defined by a generic amino acid sequence. For example, SEQ. ID No. 5 and No. 6 disclosed herein represent composite amino acid sequences of the following proteins: human OP-1, human OP-2, human OP-3, human BMP-2, human BMP-3, human BMP-4, human BMP-5, human BMP-6, human BMP-8, human BMP-9, human BMP10, human BMP-11, Drosophila 60A. Xenopus Vg-1, sea urchin UNIVIN, human CDMP-1 (mouse GDF-5), human CDMP-2 (mouse GDF-6, human BMP-13), human CDMP-3 (mouse GDF-7, human BMP-12), mouse GDF-3, human GDF-1, mouse GDF-1, chicken DORSALIN, dpp, Drosophila SCREW, mouse NODAL, mouse GDF-8, human GDF-8, mouse GDF-9, mouse GDF-10, human GDF-11, mouse GDF-11, human BMP-15, and rat BMP3b. SEQ. ID NO: 5 accommodates the C-terminal six cysteine skeleton and, SEQ. ID NO: 6 accommodates the seven cysteine skeleton.

```
Xaa Xaa Xaa Xaa Xaa Xaa Xaa Xaa Xaa Xaa Xaa Xaa Xaa Xaa Xaa Xaa SEQ. ID NO: 5
 1               5                   10                  15

Pro Xaa Xaa Xaa Xaa Xaa Xaa Xaa Cys Xaa Gly Xaa Cys Xaa Xaa Xaa Xaa
            20                  25              30

Xaa Xaa Xaa Xaa Xaa Xaa Xaa Xaa Xaa Xaa Xaa Xaa Xaa Xaa Xaa Xaa
 35              40                  45                  50

Xaa Xaa Xaa Xaa Xaa Xaa Xaa Xaa Xaa Xaa Cys Xaa Pro Xaa Xaa Xaa
            55                  60                  65

Xaa Xaa Xaa Xaa Leu Xaa Xaa Xaa Xaa Xaa Xaa Xaa Xaa Xaa Xaa
        70              75              80

Xaa Xaa Xaa Xaa Xaa Xaa Xaa Xaa Cys Xaa Cys Xaa
 85              90              95
``` wherein each Xaa is independently selected from a group of one or more specified amino acids defined as follows: "Res." means "residue" and Xaa at res. 1=(Phe, Leu or Glu); Xaa at res. 2=(Tyr, Phe, His, Arg, Thr, Lys, Gln, Val or Glu); Xaa at res. 3 (Val, Ile, Leu or Asp); Xaa at res. 4=(Ser, Asp, Glu, Asn or Phe); Xaa at res. 5=(Phe or Glu); Xaa at res. 6=(Arg, Gln, Lys, Ser, Glu, Ala or Asn); Xaa at res. 7=(Asp, Glu, Leu, Ala or Gln); Xaa at res. 8=(Leu, Val, Met, Ile or Phe); Xaa at res. 9=(Gly, His or Lys); Xaa at res. 10=(Trp or Met); Xaa at res. 11=(Gln, Leu, His, Glu, Asn, Asp, Ser or Gly); Xaa at res. 12=(Asp, Asn, Ser, Lys, Arg, Glu or His); Xaa at res. 13=(Trp or Ser); Xaa at res. 14=(Ile or Val); Xaa at res. 15=(Ile or Val); Xaa at res. 16=(Ala, Ser, Tyr or Trp); Xaa at res. 18=(Glu, Lys, Gln, Met, Pro, Leu, Arg, His or Lys); Xaa at res. 19=(Gly, Glu, Asp, Lys, Ser, Gln, Arg or Phe); Xaa at res. 20=(Tyr or Phe); Xaa at res. 21=(Ala, Ser, Gly, Met, Gln, His, Glu, Asp, Leu, Asn, Lys or Thr); Xaa at res. 22=(Ala or Pro); Xaa at res. 23=(Tyr, Phe, Asn, Ala or Arg); Xaa at res. 24=(Tyr, His, Glu, Phe or Arg); Xaa at res. 26=(Glu, Asp, Ala, Ser, Tyr, His, Lys, Arg, Gln or Gly); Xaa at res. 28=(Glu, Asp, Leu, Val, Lys, Gly, Thr, Ala or Gln); Xaa at res. 30=(Ala, Ser, Ile, Asn, Pro, Glu, Asp, Phe, Gln or Leu); Xaa at res. 31=(Phe, Tyr, Leu, Asn, Gly or Arg); Xaa at res. 32=(Pro, Ser, Ala or Val); Xaa at res. 33=(Leu, Met, Glu, Phe or Val); Xaa at res. 34=(Asn, Asp, Thr, Gly, Ala, Arg, Leu or Pro); Xaa at res. 35=(Ser, Ala, Glu, Asp, Thr, Leu, Lys, Gln or His); Xaa at res. 36=(Tyr, His, Cys, Ile, Arg, Asp, Asn, Lys, Ser, Glu or Gly); Xaa at res. 37=(Met, Leu, Phe, Val, Gly or Tyr); Xaa at res. 38=(Asn, Glu, Thr, Pro, Lys, His, Gly, Met, Val or Arg); Xaa at res. 39=(Ala, Ser, Gly, Pro or Phe); Xaa at res. 40=(Thr, Ser, Leu, Pro, His or Met); Xaa at res. 41=(Asn, Lys, Val, Thr or Gln); Xaa at res. 42=(His, Tyr or Lys); Xaa at res. 43=(Ala, Thr, Leu or Tyr); Xaa at res. 44=(Ile, Thr, Val, Phe, Tyr, Met or Pro); Xaa at res. 45=(Val, Leu, Met, Ile or His); Xaa at res. 46=(Gln, Arg or Thr); Xaa at res. 47=(Thr, Ser, Ala, Asn or His); Xaa at res. 48=Cu, Asn or Ile); Xaa at res. 49=(Val, Met, Leu, Pro or Ile); Xaa at res. 50=(His, Asn, Arg, Lys, Tyr or Gln); Xaa at res. 51=(Phe, Leu, Ser, Asn, Met, Ala, Arg, Glu, Gly or Gln); Xaa at res. 52=(Ile, Met, Leu, Val, Lys, Gln, Ala or Tyr); Xaa at res. 53=(Asn, Phe, Lys, Glu, Asp, Ala, Gln, Gly, Leu or Val); Xaa at res. 54=(Pro, Asn, Ser, Val or Asp); Xaa at res. 55=(Glu, Asp, Asn, Lys, Arg, Ser, Gly, Thr, Gln, Pro or His); Xaa at res. 56=(Thr, His, Tyr, Ala, Ile, Lys, Asp, Ser, Gly or Arg); Xaa at res. 57=(Val, Ile, Thr, Ala, Leu or Ser); Xaa at res. 58=(Pro, Gly, Ser, Asp or Ala); Xaa at res. 59=(Lys, Leu, Pro, Ala, Ser, Glu, Arg or Gly); Xaa at res. 60=(Pro, Ala, Val, Thr or Ser); Xaa at res. 61=(Cys, Val or Ser); Xaa at res. 63=(Ala, Val or Thr); Xaa at res. 65=(Thr, Ala, Glu, Val, Gly, Asp or Tyr); Xaa at res. 66=(Gln, Lys, Glu, Arg or Val); Xaa at res. 67=(Leu, Met, Thr or Tyr); Xaa at res. 68=(Asn, Ser, Gly, Thr, Asp, Glu, Lys or Val); Xaa at res. 69=(Ala, Pro, Gly or Ser); Xaa at res. 70=(Ile, Thr, Leu or Val); Xaa at res. 71=(Ser, Pro, Ala, Thr, Asn or Gly); Xaa at res. 2=(Val, Ile, Leu or Met); Xaa at res. 74=(Tyr, Phe, Arg, Thr, Tyr or Met); Xaa at res. 75=(Phe, Tyr, His, Leu, Ile, Lys, Gln or Val); Xaa at res. 76=(Asp, Leu, Asn or Glu); Xaa at res. 77=(Asp, Ser, Arg, Asn, Glu, Ala, Lys, Gly or Pro); Xaa at res. 78=(Ser, Asn, Asp, Tyr, Ala, Gly, Gln, Met, Glu, Asn or Lys); Xaa at res. 79=(Ser, Asn, Glu, Asp, Val, Lys, Gly, Gln or Arg); Xaa at res. 80=(Asn, Lys, Thr, Pro, Val, Ile, Arg, Ser or Gln); Xaa at res. 81=(Val, Ile, Thr or Ala); Xaa at res. 82=(Ile, Asn, Val, Leu, Tyr, Asp or Ala); Xaa at res. 83=(Leu, Tyr, Lys or Ile); Xaa at res. 84=(Lys, Arg, Asn, Tyr, Phe, Thr, Glu or Gly); Xaa at res. 85=(Lys, Arg, His, Gln, Asn, Glu or Val); Xaa at res. 86=(Tyr, His, Glu or Ile); Xaa at res. 87=(Arg, Glu, Gln, Pro or Lys); Xaa at res. 88=(Asn, Asp, Ala, Glu, Gly or Lys); Xaa at res. 89=(Met or Ala); Xaa at res. 90=(Val, Ile, Ala, Thr, Ser or Lys); Xaa at res 91=(Val or Ala); Xaa at res. 92=(Arg, Lys, Gln, Asp, Glu, Val, Ala, Ser or Thr); Xaa at res. 93 (Ala, Ser, Glu, Gly, Arg or Thr); Xaa at res. 95=(Gly, Ala or Thr); Xaa at res. 97=(His, Arg, Gly, Leu or Ser). Further, after res. 53 in rBMP3b and mGDF-10 there is an Ile; after res. 54 in GDF-1 there is a T; after res. 54 in BMP3 there is a V; after res. 78 in BMP-8 and Dorsalin there is a G; after res. 37 in hGDF-1 there is Pro, Gly, Gly, Pro.

SEQ ID NO: 6 includes all of SEQ ID NO: 5 and in addition includes the following sequence (SEQ ID NO: 7) at its N-terminus:

```
Cys Xaa Xaa Xaa Xaa          SEQ ID NO: 7
 1           5
```

Accordingly, beginning with residue 6, each "Xaa" in SEQ. ID No. 6 is a specified amino acid defined as for SEQ. ID No. 5, with the distinction that each residue number described for SEQ. ID No. 5 is shifted by five in SEQ. ID No. 6. Thus, "Xaa at res. 1=(Tyr, Phe, His, Arg, Thr, Lys, Gln, Val or Glu)" in SEQ. ID No. 5 refers to Xaa at res. 6 in SEQ. ID No. 6. In SEQ. ID No. 6, Xaa at res. 2=(Lys, Arg, Gln, Ser, His, Glu, Ala, or Cys); Xaa at res. 3=(Lys, Arg, Met, Lys, Thr, Leu, Tyr, or Ala); Xaa at res. 4=(His, Gln, Arg, Lys, Thr, Leu, Val, Pro, or Tyr); and Xaa at res. 5=(Gln, Thr, His, Arg, Pro, Ser, Ala, Gln, Asn, Tyr, Lys, Asp, or Leu).

Still further, morphogenically active proteins have polypeptide chains with amino acid sequences comprising a sequence encoded by a nucleic acid that hybridizes, under low, medium or high stringency hybridization conditions, to DNA or RNA encoding reference morphogen sequences, e.g., C-terminal sequences defining the conserved seven cysteine domains of OP-1, OP-2, BMP2, BMP4, BMP5, BMP6, 60A, GDF3, GDF6, GDF7 and the like. As used herein, high stringency hybridization conditions are defined as hybridization according to known techniques in 40% formamide, 5×SSPE, 5× Denhardt's Solution, and 0.1% SDS at 37° C. overnight, and washing in 0.1×SSPE, 0.1% SDS at 50° C. Standard stringency conditions are well characterized in commercially available, standard molecular cloning texts. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984): *Nucleic Acid Hybridization* (B. D. Hames & S. J. Higgins eds. 1984); and B. Perbal, *A Practical Guide To Molecular Cloning* (1984).

As used herein, "gene expression" is understood to refer to the production of a gene product encoded by a DNA sequence of interest, including the transcription of the DNA sequence and/or translation of the mRNA transcript. It is understood that gene expression in the context of the present invention is not necessarily a consequence of direct interaction of specific proteins or factors with specific DNA sequences of the present invention, but that the reporter gene product is produced as a consequence of an inductive effect that is mediated or influenced by the presence and/or expression of Pax genes in the cells of the invention.

As used herein, "operative association" relates to a fusion of the described non-coding DNA sequences with a reporter gene in such a reading frame as to be co-transcribed, or at such a relative positioning as to be competent to modulate expression of the reporter gene.

As used herein, "vector" is understood to mean any nucleic acid comprising a nucleotide sequence of interest and competent to be incorporated into a host cell and capable of functional transcription. Such vectors include linear or circular nucleic acids, plasmids, phagemids, cosmids, YACs (yeast artificial chromosomes) and the like. Vector as used herein can be used to construct a test cell, or construct DNAs, cells and/or viruses suitable for gene therapy applications.

As used herein, "non-coding sequence" or "non-coding DNA" includes DNA sequences that are not transcribed into RNA sequence, and/or RNA sequences that are not translated into protein. This category of "non-coding sequence" has been defined for ease of reference in the application, and includes sequences occurring 5' to the ATG site of the OP-1 gene at nucleotide 3318 of SEQ. ID No. 1. Further, as used herein "5' non-coding sequence" or "5' non-coding DNA" define a gene locus upstream of or 5' to the translation start site of a reporter gene. In contrast, coding sequence means a translated and/or transcribed DNA sequence encoding a reporter gene or morphogenic protein as defined herein.

As used herein, an "OP-1-specific" or "morphogen-specific" non-coding sequence is understood to define a non-coding sequence that lies contiguous to an OP-1-specific or morphogen specific coding sequence at a gene locus under naturally-occurring conditions.

"Responsive," as defined herein, is not limited to direct interaction between elements of the invention (e.g. Pax responsive OP-1 modulating element and Pax gene products) but includes indirect effects on gene transcription or translation, for example, that are mediated or influenced by the Pax gene products.

As used herein, a "Pax responsive OP-1 modulating element" is a DNA element that is responsive to the presence of a Pax gene and/or expression of a Pax gene product. That is, expression of a gene operatively associated therewith is modulated when present in a cell together with DNA encoding a Pax gene. For example, when a reporter gene and Pax gene are co-transfected into a host cell, reporter gene expression is modulated by the presence and/or expression of an endogenous Pax gene. As discussed herein, it is contemplated that a Pax responsive modulating element(s) can be located in the 5' non-coding sequences of any morphogen as defined herein. Thus, for purposes of the present invention, a Pax responsive morphogen modulating element comprises at least all of the generic features (structural, functional, chemical) associated with a Pax responsive OP-1 modulating element, and further includes allelic, species and mutant variants thereof. A "Pax gene product" is a nucleic acid or protein product encoded by a gene which is a member of the Pax family of genes.

"Pax genes" encode a family of developmentally regulated transcription factors that have been implicated in a number of human and murine congenital disorders, as well as in tumorigenesis. These genes, also characterized as "paired box genes," are defined by the presence of an evolutionarily conserved DNA binding domain, termed the "paired domain". As demonstrated below in Example 2, Pax genes and/or their expression and/or transcription products are morphogen modulators as that group of compounds is defined herein.

Paired box genes were first identified in Drosophila as a family of related genes encoding a 128-amino acid DNA binding domain, and are expressed in temporally and spatially restricted patterns during development. The phenotypes associated with Pax gene mutations demonstrate that these gene products are critical during organogenesis. Missense mutation within the paired domain of Pax genes have been associated with congenital disorders in both mouse and man. Also, Pax genes have been demonstrated to have oncogenic potential, and, for example, a translocation involving the paired box portion of Pax 3 has been associated with a human tumor.

The consensus binding sequences for Pax 6 and Pax 2 paired domains are very similar. The Pax 6 consensus spans 20 base pairs and shares a central 10-base pair region of homology with the Pax 2 consensus consisting of TCACGC-TGA (SEQ ID NO: 15), where the dash indicates a nucleotide difference between the two sequences in this central base pair region (Epstein et al. (1994) J. Biol. Chem. 269:8355–8361, the disclosure of which is incorporated by reference herein).

The respective purified paired domain proteins exhibit high affinity for their respective consensus sequences. The Pax-6 paired domain has been shown to bind to this consensus sequence as a monomer. The paired domain, when binding to such a DNA sequence, adopts an α-helical conformation and contacts residues within a large span of the DNA molecule.

As used herein, a "Pax 2 consensus binding sequence" or "Pax 2 consensus binding element" is a nucleotide sequence which has been shown to be bound by the DNA binding protein Pax 2. The consensus sequence of the Pax 2 binding site has been determined by homology to be: G T C A C/T G C G/A T G A, as depicted in SEQ. ID No. 3. (Epstein et al., (1994) J. Biol. Chem. 269:8355–8361). A "Pax 6 consensus binding sequence" or "Pax 6 consensus binding element" is a nucleotide sequence which has been shown to be bound by the DNA binding protein Pax 6. The consensus sequence of the Pax 6 binding site has been determined by homology to be T T C A C G C A/T T G/C A N T G/T A/C N T/C, as depicted in SEQ. ID No. 2 where N=A, G, C or T. (Epstein et al. (1994) J. Biol. Chem. 269:8355–8361.) Another suitable consensus sequence for purposes of the present invention is A--TTCACGCATGA-T (SEQ ID NO: 8) or TTCACGCATGA (SEQ ID NO: 9), wherein the dashes indicate that any nucleotide can reside at that locus.

"Pax 2 or Pax 6 mediated transcription or expression" means transcription or expression of a reporter gene operatively associated with a Pax responsive modulating element, or functional equivalent thereof, as described elsewhere herein. Such transcription or expression occurs in the presence of Pax genes and/or Pax gene expression products, but their presence is not required. "Pax 2 or Pax 6 mediated transcription or expression" can involve, for example, the direct physical interaction of Pax 2 or Pax 6 gene products with the Pax 2 or Pax 6 consensus binding sequences, as defined herein above. Alternatively, "Pax mediated transcription or expression" can be modulated by compounds that can mimic the transcription or expression events otherwise associated with Pax family proteins. Such compounds are contemplated herein generally as morphogen modulators, and more specifically as Pax analogs.

As discussed elsewhere herein, "allelic, species and other sequence variants thereof" includes point mutations, insertions and deletions such as those that are naturally occurring or which can be genetically engineered into an OP-1 non-coding DNA sequence using routine methods and which do not substantially affect the regulation of a reporter gene by the OP-1 non-coding sequence. For example, one of ordinary skill in the art can use site directed mutagenesis to modify, as by deletion, for example, one or more of the OP-1 non-coding sequences described herein without substantially affecting the regulation of OP-1 or a reporter gene by the modification. Such modifications are considered to be within the scope of the disclosure provided herein.

As discussed elsewhere herein, "analog" or "variant" is intended to mean a DNA or a protein which mimics or performs similar functions relative to a naturally-occurring or representative DNA or protein. For example, a DNA that is responsive to Pax 2 or Pax 6 in the same manner as those described herein, yet are structurally different therefrom, are considered DNA analogs or DNA variants within the scope of this invention. Similarly, any expression product which can modulate OP-1 expression in the same manner as Pax 2 and/or Pax 6 as disclosed herein, are considered Pax 2 and/or Pax 2 analogs or variants within the scope of this invention.

"Co-transfection" refers to the simultaneous or sequential transfection of two or more vectors into a given cell.

Where a cell line is to be established, particularly where the transfected DNA is to be incorporated into the cell's genome, lines that can be immortalized are especially desirable. As used herein, "immortalized" cell lines are viable for multiple passages without significant reduction in growth rate or protein production. It is contemplated that the cells of the present invention have utility for cell mediated gene therapy, where cells producing high levels of a reporter gene such as OP-1 are desired. It is further contemplated that the Pax consensus binding sequences or other useful sequences can be altered or adapted for viral mediated gene therapy using routine methods.

The Pax genes and/or gene products as used herein are capable of stimulating the transcription of a morphogen gene and are herein also referred to as "morphogen stimulators", "morphogen modulating compounds" or "OP-1 modulating compounds."

A "candidate compound" is any test substance that can be used to treat the cells of the present invention in vitro, in vivo or ex vivo to determine their usefulness as OP-1 modulating compounds. Accordingly, and in keeping with the earlier definition, a candidate compound which can modulate OP-1 expression in the manner of Pax 2 and/or Pax 6 as disclosed herein, is also a morphogen stimulator as well as a Pax 2 and/or Pax 6 analog. Conversely, a candidate compound which acts contrary to Pax 2 and/or Pax 6 as disclosed herein, is a morphogen suppressor or Pax 2/Pax 6 antagonist.

The OP-1 Upstream Region Contains a Silencer of Gene Expression

The presence of a sequence within the OP-1 upstream region that reduces OP-1 gene expression (a silencer fragment) was identified in expression assays described below in Example 9. The approximately 0.1 kb AatII-PvuII fragment (approximately nucleotides 2606–2690 of SEQ ID NO: 1) reduces OP-1 expression by approximately three fold (between approximately two fold and five fold in the experiments described in Example 9).

In a preferred embodiment of the invention, expression of OP-1 is increased by removing the silencer fragment from the OP-1 upstream region. In one embodiment, the silencer fragment is removed from a plasmid or other recombinant construct containing the OP-1 gene. In an alternative embodiment, a recombinant cell line is made wherein one or both genomic copies of the OP-1 gene are modified to remove the silencer fragment, using methods known in the art.

In another embodiment of the invention, the silencer fragment is used to modulate the expression of another (non-OP-1) gene. One or more copies of the silencer fragment are inserted in the promoter region of the gene in order to reduce expression. The silencer fragment is inserted into the promoter region of a gene that is contained in a plasmid, a recombinant vector, or in the genome itself.

The silencer fragment contained within the AatII-PvuII fragment can be more precisely identified by standard deletion analysis of the fragment using the expression assay described in Examples 2 and 9. Truncated silencer fragments, identified by a further deletion analysis, are also useful in the invention.

A naturally occurring sequence variant of the silencer fragment (or of a truncated silencer fragment), or a nucleic acid which hybridizes to the silencer fragment (or to a truncated siencer fragment) under high stringency hybridization conditions, is also useful in the invention.

Exemplary Cells, Vectors, Reporter Genes and Assays for Use in Screening Compounds Which Modulate OP-1 Gene Expression A. Useful Cells Any eukaryotic cell, including an immortalized cell line suitable for long term culturing conditions, is contemplated to be useful for the methods and cells of the invention. Useful cells should be easy to transfect, are capable of stably maintaining foreign DNA with an unrearranged sequence, and have the necessary cellular components for efficient transcription and translation of the protein, including any elements required for post-translational modification and secretion, if necessary. Where the cell is to be transfected with a non-dominating selection gene, the cell genotype preferably is deficient for the endogenous selection gene. Preferably, the cell line also has simple media composition requirements, and rapid generation times. Useful cell lines are mammalian cell lines, including myeloma, HeLa, fibroblast, embryonic and various tissue cell lines, e.g., kidney, liver, lung and the like. The cells may be derived from tissue or subcultured from established cell lines. As used herein, "derived" means the cells are from the cultured tissue itself or are a cell line whose parent cells are of the tissue itself. Cell lines particularly useful in practicing the present invention are, for example, Y79 human retinoblastoma cells, G401 human kidney cells, ROS human osteoblastic cells, MCF-7 human mammary cancer cells and LLCBK1 porcine proximal tubule cells. A large number of cell lines now are available through the American Type Culture Collection (Rockville, Md.) or through the European Collection of Animal Cell Cultures (Porton Down, Salisbury, SP4 0JG, U.K.)

Where the expression of a reporter gene that is controlled by non-coding sequences of the morphogen OP-1 is to be analyzed, particularly useful cells and cell lines are envisioned to include eukaryotic, preferably mammalian cells of a tissue and cell type known to express OP-1 and/or closely related proteins. See, for example, Ozkaynak, et al. (1991), Biochem. Biophys. Res. Commun. 179: 116–123 for a detailed description of tissues known to express OP-1. Such cells, include, without limitation, cells of uro-genital cell origin, including kidney, bladder and ovary cells, lung, liver, bone, nerve, mammary gland and cardiac cells, cells of gonadal origin, cells of gastrointestinal origin, glial cells and other cell lines known to express endogenous genes encoding morphogenic proteins. Preferred cell lines are of epithelial origin.

Cell cultures of kidney, adrenals, urinary bladder, brain, or other organs, can be prepared as described widely in the literature. For example, kidneys can be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues can be established in multiwell plates (6 well or 24 well) according to conventional cell culture techniques, and are cultured in the absence or presence of serum for a period of time (1–7 days). Cells can be cultured, for example, in DMEM containing 10% fetal calf serum or in serum-deprived medium or in defined medium (e.g., containing insulin, transferrin, glucose, albumin, or other growth factors). Test compounds are added to the cultured cells and OP-1 biosynthesis monitored and measured at various time points using the methods described previously herein. Suitable cell lines include cell lines that have been shown to contain high levels of OP-1 mRNA, indicating that the OP-1 promoter is active in the cells. Cells and their culture fluids are assayed using techniques well known in the art, either for mRNA levels, using Northern blot analysis and OP-1 mRNA specific probes, or for protein levels, using OP-1 specific antibodies. For example, OP-1 protein can be measured on a tissue section or cell directly using standard immunofluorescence techniques or in culture fluids and body fluids using a sandwich immunoassay. Other methods for detecting, measuring and purifying proteins are well know in the art.

Alternatively, in one aspect the present invention may be practiced in yeast cells such as S. cerevisiae to identify or further characterize protein-protein interactions of the identified intracellular OP-1 modulating factors of the present invention. For example, the yeast two hybrid system, as described in Kalpana et al. (1993) 90 Proc. Natl. Acad. Sci. USA. (22): 10593–10597 and already well known to those skilled in the art, is useful for delineating domains or critical residues for an interaction between two proteins, for example, a protein X and a protein Y. Briefly, hybrid genes are constructed for expression in yeast comprising (a) a DNA binding domain fused to a protein X and (b) an activator domain fused to a protein Y. Transcriptional activation in these experiments is only restored when protein X interacts with protein Y leading to close contact of both the binding domain and the activation domain. Transcription activation is then monitored by a reporter gene resident in the yeast strain.

B. Exemplary Vectors/Vector Construction Considerations

Useful vectors for use in the invention include, but are not limited to plasmids, cosmids, phagemids, yeast artificial chromosomes or other large vectors. Vectors that can be maintained within the nucleus or integrated into the genome by homologous recombination are also useful.

Selected portions of noncoding OP-1 sequence can be cloned into a useful vector using standard molecular cloning techniques, as exemplified below. Restriction endonuclease sites will be utilized when possible, and can be engineered into the sequence when needed. Restriction endonuclease sites can be engineered into the non-coding sequence using the common techniques such as site directed mutagenesis and PCR with primers including the desired restriction endonuclease site.

Also envisioned is a nucleic acid construct comprising a small fragment of 5' non-coding OP-1 sequence in combination with additional conserved elements such as one or more Pax 6 binding sequences and/or Pax 2 binding sequences in operative association with a reporter gene.

A range of useful 5' non-coding fragments is provided herein, and as will be apparent to those of ordinary skill in the art, smaller fragments of OP-1 sequence also are useful. Such smaller fragments can be identified by deleting bases from one or both ends of the provided 5' noncoding fragments, using techniques that are well known in the art and testing the truncated constructs for their ability to modulate reporter gene expression. In this way, the shortest modulating sequences can be identified.

C. Transfection Considerations

Any routine method for incorporating nucleic acids into cells of interest is contemplated in the method of the invention. For example, calcium phosphate ($CaPO_4$), followed by glycerol shock is a standard means used in the art for introducing vectors, particularly plasmid DNA into mammalian cells. A representative method is disclosed in Cockett et al., (1990) Biotechnology 8:662–667, incorporated herein by reference. Other methods that may be used include electroporation, protoplast fusion (particularly useful in myeloma transfections), microinjections, lipofections and DEAE-dextran mediated uptake. Methods for these procedures are described in F. M. Ausubel, ed., Current Protocols in Molecular Biology, John Wiley & Sons, New York (1989). An important aspect of the invention is the DNA sequences with which the cell is transfected, rather than the mechanical or chemical process by which the DNA incorporation is accomplished.

As will be appreciated by those having skill in the art, optimal DNA concentrations per transfection and other standard conditions will vary according to the transfection protocol. For calcium phosphate transfection, for example, preferably 5–10 μg plasmid DNA per plasmid type is transfected. In addition, the DNA to be transfected preferably is essentially free of contaminants that may interfere with DNA incorporation. A standard means used in the art for purifying DNA is by ethidium bromide banding.

D. Exemplary Reporter Genes

Reporter genes are characterized as being easy to transfect into a suitable host cell, easy to detect using an established assay protocol, and genes whose expression can be tightly regulated. Other reporter genes contemplated to have utility include, without limitation, the luciferase gene, the Green Fluorescent Protein (GFP) gene, human growth hormone, GAL4 and β-galactosidase.

A well-recognized reporter system is the firefly luciferase reporter system. See, for example Gould, S. J., and Subramani, S. (1988) Anal. Biochem., 7:404–408 for a description of the reporter gene and general methodology. The luciferase assay is fast and has increased sensitivity. Further, the half-life of luciferase protein is short and therefore allows for accurate kinetic studies of luciferase production. The system also is particularly useful in bulk transfections or if the promoter of interest is weak. In this assay transfected cells are grown under standard conditions, and when cultured under assay conditions both ATP and the substrate luciferin is added to the cell lysate. The enzyme luciferase catalyzes a rapid, ATP dependent oxidation of the substrate which then emits light. The total light output is measured using a luminometer according to manufacturer's instructions (e.g., Promega) and is proportional to the amount of luciferase present over a wide range of enzyme concentrations. For example, a vector such as pGL2-LUC (Promega) is particularly useful.

A second well-known reporter system is based on immunologic detection of hGH, it is quick and easy to use. (Selden, R., Burke-Howie, K. Rowe, M. E., Goodman, H. M., and Moore, D. D. (1986), Mol. Cell Biol., 6:3173–3179 incorporated herein by reference). hGH is assayed in the media, rather than in cell extracts. This allows direct monitoring over by a single population of transfected cells over time.

Additional useful reporter genes are any well characterized genes the expression of which is readily assayed, and examples of such reporter genes can be found in, for example, F. A. Ausubel et al., Eds., Current Protocols in Molecular Biology, John Wiley & Sons, New York, (1989).

As will be appreciated by those having ordinary skill in the art, the listed reporter genes are only a few of the possible reporter genes, and it is only for ease of description that all available reporter genes are not listed. It will be apparent to those of ordinary skill in the art that genes encoding other detectable proteins of interest, such as the gene encoding human OP-1 shown in SEQ. ID No. 1, or other morphogen whose enhanced expression is desirable, is also within the scope of a suitable reporter gene.

As indicated above and as will be appreciated by those having ordinary skill in the art, particular details of the conventional means for transfection, expression, and assay of recombinant genes are well documented and are understood by those having ordinary skill in the art. The instant invention enables and discloses vectors, cells and a method for screening compounds to determine the capability of compounds to modulate the expression of OP-1 via the non-coding sequences of the OP-1 genomic DNA.

Further details on the various technical aspects of each of the steps used in recombinant production of foreign genes in mammalian expression systems can be found in a number of texts and laboratory manuals in the art, such as, for example, F. M. Ausubel et al., Ed., Current Protocols in Molecular Biology, John Wiley & Sons, New York, (1989).

In view of this disclosure and the examples provided below, a method for identifying molecules which can affect OP-1 expression in a particular cell type in vivo now is provided.

EXAMPLE 1

Cloning of Human OP-1 Gene Non-Coding Sequences

Human OP-1 upstream non-coding sequence was obtained by screening the human genomic library, HL 1067J. (Clontech). The library was screened by an initial plating of 750,000 plaques (approximately 50,000 plaques/plate). Hybridizations were done in 40% formamide, 5×SSPE, 5×Denhardt's solution, and 0.1% SDS at 37° C. using a $^{32}$P-labeled probe made from a human 0.47 kb EcoRI OP-1 cDNA fragment containing mainly 5' non-coding and exon 1 sequences. Nonspecific counts were removed in 0.1×SSPE, 0.1% SDS by shaking at 50° C.

A 7 kb EcoRI fragment from the human genomic clone, lambda Ö3, was isolated and sequenced and contained 5 kb of OP-1 upstream non-coding sequence.

All sequencing was done according to Sanger et al. (1977) Proc. Natl. Acad. Sci. 14:5463–5467, using exonuclease III-mediated unidirectional deletion (Ozkaynak et al., (1987) BioTechniques, 5:770–773), subcloning of restriction fragments, and synthetic primers. Compressions were resolved by performing the reactions at 70° C. with Taq polymerase and rising 7-deaza-GTP (U.S. Biochemical Corp., Cleveland, Ohio).

As will be discussed in more detail below, the 1–3317 region of SEQ. ID No. 1 contains a plurality of conserved DNA sequences which share homology with Pax homeobox consensus sequences of Epstein et al. (1994) J. Biol. Chem. 269:8355–8361, and have been identified and designated herein as Pax responsive OP-1 modulating elements, comprising approximately nucleotides 108–121, 139–154, 157–167, 365–378, 491–503, 497–511, 737–747, 891–903, 994–1006, 1123–1140, 1144–1161, 1285–1297, 598–613, 1750–1762, 2001–2023, 2365–2378, 2931–2944 of SEQ. ID No. 1. Particularly preferred Pax 6 responsive OP-1 modulating elements reside at approximately nucleotides 108–121, 139–154, 365–378, 497–511, 598–613, 1750–1762, 2365–2378 and 2931–2944. Other preferred Pax 6 elements include approximately 157–167, 1123–1140, 1144–1161, 1285–1297 and 2001–2023. Particularly preferred Pax 2 responsive OP-1 modulating elements reside at approximately nucleotides 491–503, 737–747, 891–903 and 994–1006.

Still other preferred Pax 6 responsive OP-1 modulating elements reside at approximately 104–120, 105–121, 142–158, 362–378, 497–513, 1750–1766, 2362–2378, 2928–2944, 1128–1144, 1125–1141, 1143–1159, 2000–2016, 2003–20019, 2007–2023, 601–617, 595–611, and 1746–1762. Still other preferred Pax 2 responsive OP-1 modulating elements reside at approximately 493–503, 891–901 and 996–1006.

The transcription initiation site for the human OP-1 gene is at base 2790 of SEQ. ID No. 1. The OP-1 protein translation initiation site is nucleotide 3318 of SEQ. ID No. 1.

As described above, osteogenic protein-1 plays a critical role in modulating mesenchymal differentiation and inducing the process of cartilage and bone formation. It is also required for kidney development and is shown to prevent kidney damage from ischemia/reperfusion injury in rats. As presented below in Example 2, functional analysis of the human OP-1 gene promoter has been carried out. The OP-1 promoter and 5' truncated versions of it were placed upstream of the luciferase coding region which served as the reporter gene. In certain embodiments, the results of the luciferase assays after transient transfection of these constructs into a human kidney cell line, G401, indicate that this upstream sequence has promoter activity. This activity resides about 300 to 700 nucleotides upstream of the first ATG of the OP-1 gene. This promoter activity is constitutive and is not influenced by transactivating agents, e.g., Pax 2 and Pax 6 (see FIG. 1B) which are involved in epithelial/mesenchymal interactions during tissue morphogenesis. In other embodiments drawn to the region between 700 to 3300 nucleotides upstream of the OP-1 gene, however, the data indicate the presence of potential silencer elements of the promoter. Moreover, this region of the promoter can be influenced by a host of factors, including Pax 2, Pax 6 and Retinoic Acid, as illustrated in Example 2.

Both transient and permanent G401 cell lines containing the below-described constructs have been isolated and tested. Other host cell lines including Human Retinoblastoma Y79, Rat Osteosarcoma ROS and Porcine Proximal Tubule LLCPK1 have been tested in transient transfection assays. These data are expected to illustrate similar Pax-mediated regulatory considerations and tissue specificity, thereby permitting even further identification of tissue- and developmental-specific morphogen modulators.

EXAMPLE 2

Analysis of OP-1 Gene Expression

In one aspect, this invention presents a method in which OP-1 non-coding sequences are assayed while in operative association with a reporter gene and modulator compounds such as Pax 2 or Pax 6 or analogs thereof, are thereby tested for their influence on the expression of OP-1. For example, non-coding sequences which are involved in the modulation of OP-1 expression via Pax gene products or functional equivalents or analogs thereof will be identified by (1) transfecting a cell with one or more Pax protein expression vectors and an expression vector comprising OP-1 non-coding sequences in operative association with a reporter gene; (2) culturing the transfectants with one or more candidate compounds; (3) measuring the level of reporter gene expression; and (4) comparing this level of expression to the level of reporter gene expression in the absence of the compound(s). Alternatively, non-coding sequences can be assayed for their responsiveness to compounds which can mimic Pax 2 and/or Pax 6, i.e., Pax 2 and/or Pax 6 analogs. The protocol of the present invention is based on a procedure for identifying compounds which alter, either directly or indirectly, endogenous levels of morphogen expression.

It is also contemplated that candidate compounds may be administered in vivo to modulate the level of an endogenous protein, such as OP-1. This can be accomplished by detection of the expression product either at the protein or RNA level.

Cultured cells are transfected with portions of OP-1 non-coding sequences in operative association with a reporter gene, and such transfected cells are maintained with the vector remaining as a plasmid in the cell nucleus, or the vector can be integrated into the host cell genome, preferably at the OP-1 genomic locus. Cell samples for testing the level of reporter gene expression are collected periodically and evaluated for reporter gene expression using the appropriate assay for the given reporter gene as indicated in the section describing reporter gene assays, or, alternatively, a portion of the cell culture itself can be collected periodically and used to prepare polyA(+) RNA for mRNA analysis. For example, to ascertain the particular time point at which OP-1 is produced following treatment with a candidate morphogen, cells treated with the candidate OP-1 modulating compound, cells treated with compound are collected periodically and evaluated for OP-1 production, as described above. To monitor de novo OP-1 synthesis, some cultures are labeled according to conventional procedures with an $^{35}$S-methionine/$^{35}$S-cysteine mixture for 6–24 hours and then evaluated to quantitate OP-1 synthesis by conventional immunoassay methods. Alternatively, anti-OP-1 antibodies can be labeled and incubated with the cells or cell lysates, and the bound complexes detected and quantitated by conventional means, such as those described herein above. Tissues can also be examined directly for the synthesis of OP-1 mRNA using the art-recognized technique of in situ hybridization.

Once candidate compounds are identified, they can be produced in reasonable, useful quantities using standard methodologies known in the art. Amino acid-based molecules can be encoded by synthetic nucleic acid molecules, and expressed in a recombinant expression system as described herein above or in the art. Alternatively, such molecules can be chemically synthesized, e.g., by means of an automated peptide synthesizer, for example. Non-amino acid-based molecules can be produced by standard organic chemical synthesis procedures.

Morphogen agonists are anticipated to have utility in any application where tissue morphogenesis is desired, such as in the regeneration of damaged tissue resulting from mechanical or chemical trauma, degenerative diseases, tissue destruction resulting from chronic inflammation, cirrhosis, inflammatory diseases, cancer and the like, and in the regeneration of tissues, organs and limbs. Morphogen antagonists are envisioned to have utility in applications where tissue morphogenesis is to be limited as, for example, in the treatment of malignant transformations including, but not limited to, osteosarcomas, Paget's disease, and fibrodysplasia ossificans progressiva (See, for example, Roush (1996) *Science* 273:1170). The ability to detect OP-1 protein in solution provides a valuable tool for diagnostic assays, allowing us to monitor the levels of OP-1 free in the body, e.g., in serum, urine, spinal or peritoneal fluid, breast exudate, and other body fluids in order to assess the presence of OP-1 modulating activity. The present invention therefor provides a means of identifying naturally occurring or synthetic proteins or other factors or drugs that have OP-1 modulating activities. Moreover, compounds that induce the expression of Pax 2 or Pax 6 are also particularly useful.

OP-1 is expressed in a variety of different cell types, including renal, bone, lung, heart, uterine, cardiac and neural tissue. Candidate compounds can be identified which have a modulating effect on cells of one tissue type but not another, and/or wherein the effect is modulated differently in the different cells. The assay described below can be used to evaluate the effect of a candidate compound in a particular cell type known to express OP-1 under physiological conditions.

The present invention therefor also provides a test cell or cell line which expresses an exogenously introduced OP-1 protein, which is responsive to morphogen modulators such as Pax 2 and/or Pax 6 or analogs thereof as contemplated herein. Said cell or cell line can be also used as described herein, to replace cell lines that produce OP-1 endogenously, for the screening assays described herein above. Further, the invention provides a test cell that is transfected with DNA encoding Pax gene products (e.g., Pax 2 and/or Pax 6) for the modulation of endogenous or exogenous OP-1 gene expression.

While a readily assayable, well characterized, non OP-1 reporter gene is preferred in the screening method disclosed herein, as will be appreciated by those having ordinary skill in the art, OP-1 coding sequence also may be used in the method of the invention providing an improved method for the production of high levels of OP-1, exploiting the high level of induction of gene expression of the present invention. The OP-1 expression preferably is determined by an immunoassay or by Northern or dot blot or other means for measuring mRNA transcript. See, for example, WO 95/11983, published May 4, 1995 for a detailed description on assaying changes in OP-1 levels in a cell or fluid. Further, the cells of the present invention can be used in the analysis of the transcription factors, for example, DNA-protein and/or protein-protein interactions involved in OP-1 transcription regulation or that of other morphogens.

Provided below is an exemplary protocol for carrying out the method of the invention, using the luciferase gene as the reporter gene and a mammalian cell line known to express OP-1. The example is non-limiting, and other cells, reporter genes and morphogen non-coding sequences such as, but not limited to, an OP-1 non-coding sequence, are envisioned.

The OP-1 genomic DNA nucleotides 1–3317 of SEQ. ID No. 1 was used to prepare a series of deletion constructs carrying the luciferase reporter gene and portions of the OP-1 gene non-coding region (FIG. 1A). The pGL2-Basic plasmid comprising a nucleotide sequence encoding the detectable enzyme luciferase (Promega, Madison Wis.) was employed as the basic vector. The OP-1 promoter sequence (corresponding to nucleotides 1 to 3305 of SEQ ID No. 1) was then inserted into the pGL2-Basic plasmid (construct pAS3.3, FIG. 1A). Nucleotide +1 is 30 nucleotides downstream of the Hind III site present in the OP-1 genomic sequence. There are therefore an additional 30 base pairs of DNA sequence upstream of position +1 in the OP-1 promotor, comprising AAGCTTGATG CCTGCACAGT CAGCCCTCAG (SEQ ID NO: 10), wherein AAGCTT corresponds to a Hind III site.

The genomic sequence was digested with Hind III and BamHI. The BamHI site was introduced into the OP-1 promoter at nucleotides 3306 to 3311 of SEQ. ID No. 1 by site-directed mutagenesis according to methods well known in the art using the following reverse complement primer: 5' CAT CGC GCC GGA TCC ACG CGC TAC CCG GGC 3' (SEQ ID NO: 11) wherein GGATCC corresponds to a BamHI site.

Thus the mutagenesis generated the following change in the OP-1 sequence:

native seq: 5' GCC CGG GTA GCG CGT AGA GCC GGC GCG ATG 3' (SEQ ID NO: 12)

altered seq: 5' GCC CGG GTA GCG CGT GGA TCC GGC GCG ATG 3' (SEQ ID NO: 13)

This resulted in the following changes in the OP-1 promotor in construct pAS3.3: GCCCGGGTAG CGCGTGGATC TAAGTAAGCT TGGCATTCCG GTACTGTTGG TAAA ATG (SEQ ID NO: 14) wherein the G represents nucleotide 3306 of SEQ. ID No. 1 and wherein ATG corresponds to the luciferase ATG (nucleotides 3318 to 3320 of SEQ. ID No. 1).

Therefore, the native OP-1 promoter sequences stop at nucleotide 3305, nucleotide 3306 results from an A to G nucleotide change, and nucleotides 3307 to 3345 are derived from the pGL2-Basic vector. Thus, 3335 nucleotides (30 nucleotides upstream of nucleotide 1 up to 3305 of SEQ. ID No. 1) of cloned 5' non-coding sequence of the OP-1 gene was placed in transcriptionally operative association with the luciferase reporter gene.

Serial 5' deletions (FIG. 1A) were constructed by digestion of the pAS3.3 construct with a series of restriction enzymes followed by religation of the plasmid according to well-known cloning techniques. For example, the pAS3.3 vector was cleaved with BglII (present in the pGL2-Basic vector and in the OP-1 promoter) and recircularized to obtain pAS2.5; the pAS3.3 vector was cleaved with KpnI (present in the pGL2-Basic vector and in the OP-1 promoter) and recircularized to obtain pAS1.2; the pAS3.3 vector was cleaved with XhoI (present in the pGL2-Basic vector) and SacII, followed by a T4 DNA polymerase fill-in reaction and recircularized to obtain pAS0.8; the pAS3.3 vector was cleaved with KpnI (present in the pGL2-Basic vector) and AatII followed by a T4 DNA polymerase fill-in reaction and recircularized to obtain pAS0.7; the pAS3.3 vector was cleaved with XhoI (present in the pGL2-Basic vector) and PvuII followed by a T4 DNA polymerase fill-in reaction and recircularized to obtain pAS0.6; the pAS3.3 vector was cleaved with XhoI (present in the pGL2-Basic vector) and AvrII followed by a T4 DNA polymerase fill-in reaction and recircularized to obtain pAS0.3; and the pAS3.3 vector was cleaved with KpnI (present in the pGL2-Basic vector) and PstI followed by a T4 DNA polymerase fill-in reaction and recircularized to obtain pAS0.1.

The vectors were transfected into G401 human kidney cells, either alone or together with the cDNA for human Pax 2 and/or for human Pax 6, previously cloned into a pCMVβ expression vector (Clonetech), with the removal of the β-galactosidase gene by standard methods (Epstein, et al. (1994) J. Biol. Chem. 269:8355–8361), the disclosure of which is incorporated herein by reference. Briefly, cells were plated in 60 mm petri dishes ($5 \times 10^5$ cell/dish) in McCoy's 5A medium containing 10% fetal bovine serum. Twenty-four hours later, the above-described vectors were transfected into the cultured cells, using a Lipofectamine (BRL/Gibco) method in serum-free medium (Optimem, BRL) for 6 hours. Cells were transfected with (a) an OP-1 promoter constructs alone; (b) an OP-1 promoter construct+the Pax 2 construct; (c) an OP-1 promoter construct+the Pax 6 construct; or (d) an OP-1 promoter construct+the Pax 2 construct+the Pax 6 construct. Control transfected cells contained the pGL-Basic plasmid without OP-1 non-coding sequences as a negative control and pSV-Luc, which has an SV40 promoter, as a positive control. Thereafter, transfected cells were cultured in complete media Seventy-two hours later, luciferase activity was measured using the Promega Luciferase Assay System (Promega, Madison Wis.) and a luminometer (DynaTech). The results are displayed in FIG. 1B and discussed below.

The luciferase production by cells containing the pAS3.3 construct, comprising 3305 nucleotides upstream of the translation start site of the OP-1 gene, was induced 2.4 fold by co-transfection with the Pax 2 cDNA and 9.6 fold by co-transfection with the Pax 6 cDNA (FIG. 1B). The triple transfection of both the Pax 2 and Pax 6 expression vectors with the pAS3.3 construct resulted in an additive 11.5 fold induction suggesting that Pax 2 and Pax 6 gene products have an additive effect on OP-1 gene expression. Cells containing the 5' deletion mutants of the pAS3.3 construct were less responsive to the inductive effect of co-transfection with Pax 2 or Pax 6 constructs. For example, the pAS2.5 construct was only induced 1.7 fold by co-transfection with the Pax 2 construct and this Pax 2 responsiveness was abolished by further deletion of about 1.3 kb of 5' sequence, with no Pax 2 induction detected for the pAS1.2 construct or the remaining constructs with further 5' deletions.

Pax 6 responsiveness was also lost by about 42% upon deletion of 793 bases from the pAS3.3 construct A 4 to 5.5 fold induction of luciferase production was demonstrated in the cells comprising the Pax 6 construct co-transfected with pAS2.5 (+794 to +3305), pAS1.2 (+2068 to +3305), pAS0.8 (+2501 to +3305), and pAS0.7 (+2606 to +3305) of SEQ. ID No. 1 but this Pax 6 responsiveness was lost upon deletion of nucleotides +2606 to +2690. This suggests that this 85 nucleotide region contains preferred sequences necessary for OP-1 modulation by Pax gene products or analogs thereof.

Constructs pAS3.3 and pAS2.5, comprising 3.3 kb 5' non-coding region (1 to 3305 of SEQ. ID No. 1) and a 793 nucleotide 5' deletion thereof, respectively, produced less luciferase constitutively than the other deletion mutants, suggesting the presence of negative regulatory elements in the 5' non-coding region comprising nucleotides 1 to 2067 (FIG. 1B).

The complete DNA sequence of the 5' noncoding upstream OP-1 gene (1 to 3317 of SEQ. ID No. 1) was analyzed using a string search program to identify putative Pax 2 or Pax 6 binding motifs, relying in part on the Pax 2 and Pax 6 consensus sequences described by Epstein et al. (1994) *J. Biol. Chem.* 269:8355–8361, and in part on certain other suitable Pax consensus sequences disclosed herein. One consensus sequence for Pax 6 is T T C A C G C A/T T G/C A N T G/T A/C N T/C corresponding to SEQ. ID No. 2 wherein the N is either A, G, C or T. One consensus sequence for Pax 2 is G T C A C/T G C G/A T G A and corresponds to SEQ. ID No. 3. The string search program allowed for partial mismatches and revealed a number of Pax 6 or Pax 2 responsive regions. Currently preferred Pax 2 responsive regions are located at approximately 491–503, 737–747, 891–903, 994–1006 of SEQ. ID No. 1 and share approximately 69–82% identity with the Pax 2 consensus sequence of SEQ. ID. No. 3.

Currently preferred Pax 6 responsive elements include approximately nucleotides 108–121, 139–154, 365–378, 497–511, 1750–1762, 2365–2378, 2931–2944 of SEQ. ID No. 1. These Pax 6 responsive elements share between 53% and 82% identity with the Pax 6 consensus sequence of SEQ. ID No. 3. Other currently preferred Pax 6 responsive elements include approximately nucleotides 157–167, 1123–1140, 1144–1161, 1285–1297, and 2001–2023 of SEQ. ID No. 1.

It is understood that some of the consensus Pax motifs may function to regulate OP-1 gene expression, where others may not. Further, characterization of each putative Pax responsive OP-1 element is accomplished as described below in Example 5. As earlier discussed, it is contemplated that Pax responsive elements, such as those described herein, are present in the promoter sequences of other morphogens as defined herein and thereby can be identified and exploited as taught herein. Pax responsive elements, as contemplated by the present invention, modulate the in vivo, ex vivo and in vitro expression of morphogens and thus are useful for identifying particular compounds that can modulate particular morphogens.

It is contemplated that the present invention further provides a useful method for identifying nucleic acids and their respective encoded compounds capable of modulating Pax mediated OP-1 gene regulation. In one embodiment, one or more candidate nucleic acids which encode a candidate compound or compounds capable of intracellular modulation of OP-1 gene expression, mediated directly or indirectly by Pax responsive elements located in the OP-1 gene 5' non-coding region (nucleotides 1–3317 of SEQ. ID No. 1), are also transfected into the cells of the invention comprising Pax responsive OP-1 5' non-coding sequence/reporter gene vectors. "Candidate nucleic acid" or "candidate DNA" or "candidate RNA" as defined herein, is therefor a nucleic acid (e.g. a DNA or RNA) that encodes a compound that modulates OP-1 gene expression via a Pax responsive element. In one embodiment, a candidate DNA can encode a transcription factor that shares functional similarity with a Pax gene product or is a Pax analog or agonist. Alternatively, the candidate nucleic acid can encode a compound that behaves as an inhibitor of OP-1 gene expression or is a Pax antagonist. In another embodiment, a candidate RNA or RNAs may be first isolated from a cell or synthesized in vitro by methods well known to the skilled artisan and then used to transfect the above-described cell. It is also, contemplated that tissue specific candidate nucleic acids can be identified and isolated according to the method of the present invention. Thus, for example, expression vectors comprising tissue specific candidate DNAs can be co-transfected into a cell together with an expression vector containing the OP-1 5' non-coding sequence of nucleotides 1–3317 of SEQ ID No 1, or truncated versions thereof, in operative association with a luciferase reporter gene. Alterations in luciferase activity relative to control transfections is an indication that the candidate DNA encodes a compound capable of modulating OP-1 gene regulation. It is contemplated that individual nucleic acids or pools of nucleic acids, for example, a cDNA library or a pool of synthetic RNAs, may be screened for their ability to modulate OP-1 gene expression via the responsive elements of the present invention in accordance with the methods of the invention.

EXAMPLE 3

Further Characterization of the Pax Responsive OP-1 Modulating Elements

To characterize the respective roles of certain of the Pax 2 (for example, approximately, nucleotides 491–503, 737–747, 891–903, 994–1006 of SEQ. ID No. 1) and Pax 6 responsive elements (for example, approximately, nucleotides 108–121, 139–154, 157–167, 365–378, 498–511, 598–613, 1123–1140, 1144–1161, 1285–1297, 1750–1762, 2001–2023, 2365–2378, 2931–2944 of SEQ. ID No. 1) in the modulation of the OP-1 gene expression, mutations of the various Pax 2 and Pax 6 responsive elements are analyzed. A loss or decrease of Pax mediated OP-1 gene expression by mutation of a portion of each Pax 2 responsive element sequence indicates a role for that sequence in Pax mediated OP-1 gene regulation. Conversely, an increase in Pax mediated OP-1 gene expression of the mutated Pax responsive elements may indicate, for example, enhanced binding of Pax transcription factors to the altered DNA recognition sequence or, alternatively, a loss or decrease in binding of one or more negative regulatory elements.

Further, the OP-1 gene promoter is analyzed by DNase footprinting to further define the Pax responsive regions and to determine binding specificity and affinity of the Pax gene products required for the expression of the OP-1 gene. DNase footprinting is carried out according to techniques well known to those skilled in the art.

In addition, the interaction of the OP-1 promoter with nuclear proteins is further characterized by gel shift assays using oligonucleotides probes corresponding to the Pax 2 consensus sequence (SEQ. ID No. 3) or the Pax 6 consensus sequence (SEQ. ID No. 2) or variants thereof, with and without mutations in the oligonucleotide sequences. Briefly, cells are lysed according to art known methods and nuclear extracts are prepared and incubated with a radiolabelled oligonucleotide of choice, by methods well known to the skilled artisan. Binding of one or more of the protein components of the extract to the oligonucleotide produces DNA/protein complexes having retarded electrophoretic mobility relative to the mobility of the uncomplexed oligonucleotide DNA probe. Completion of radiolabelled oligonucleotide binding with cold (unlabelled) oligonucleotide is performed to confirm the specificity of DNA/protein complexes. These assays can demonstrate alterations in the amount or activity of a nuclear extract component in response to treatment with candidate compounds.

Supershift assays, in which the nuclear extract oligonucleotide complexes are further retarded by complexing with specific antibody, are used to determine the identity of the Pax gene product or analog thereof. In these assays, the previously described protein-oligonucleotide probe complexes are farther incubated with specific antibody and subjected to electrophoresis, according to art known methods. The DNA-protein complexes from a test cell induced, for example, by a candidate compound, are supershifted during gel analysis when treated with an anti-Pax 2 or anti-Pax 6 antibody, or other Pax family antibodies, for example. This supershift can be reversed by incubation with the antigenic peptide.

The tissue specificity of the Pax-DNA complexes is further defined by a comparison of gel shift and supershift mobilities using cell extracts from various tissues and cells. These studies may reveal the involvement of one or more tissue specific factors that may participate in Pax mediated regulation of OP-1 gene transcription.

EXAMPLE 4

In vivo Animal Model for Testing Efficacy of Compounds to Modulate OP1 Expression It previously has been demonstrated that OP-1 can be an effective treatment for osteoporosis on the standard ovariectomized rat model, as indicated by the dose-response increase in alkaline phosphatase and osteocalcin levels following injection with OP-1. The osteoporotic rat model provides an in vivo model for evaluating the efficacy of a candidate compound for modulating morphogen synthesis. In order to determine the effect of a candidate morphogen stimulating agent on OP-1 production and, thereby, on bone production in viva, alkaline phosphatase and osteocalcin levels are measured under conditions which promote osteoporosis, e.g., wherein osteoporosis is induced by ovary removal in rats and in the presence and absence of a candidate compound. A compound competent to enhance or induce endogenous OP-1 expression should result in increased osteocalcin and alkaline phosphatase levels.

Forty Long-Evans rats (Charles River Laboratories, Wilmington) weighing about 200 g each are ovariectomized (OVX) using standard surgical procedures, and ten rats are sham operated. The ovariectomization of the rats produces an osteoporotic condition within the rats as a result of decreased estrogen production. Food and water are provided ad libitum. Eight days after ovariectomy, the rats, prepared as described above, are divided into three groups: (a) sham-operated rats; (b) ovariectomized rats receiving 1 ml of phosphate-buffered saline (PBS) i.v. in the tail vein; and (c) ovariectomized rats receiving various dose ranges of the candidate morphogen stimulating agent either by intravenous injection through the tail vein or direct administration to kidney tissue.

The effect of the candidate compound on in vivo bone formation can be determined by preparing sections of bone tissue from the ovariectomized rats. Each rat is injected with 5 mg of tetracycline, which will stain the new bone (visualized as a yellow color by fluorescence), on the 15th and 21st day of the study, and on day 22 the rats are sacrificed. The body weights, uterine weights, serum alkaline phosphatase levels, serum calcium levels and serum osteocalcin levels then were determined for each rat. Bone sections are prepared and the distance separating each tetracycline staining is measured to determine the amount of new bone growth. The levels of OP-1 in serum following injection of the candidate agent also can be monitored on a periodic basis using routine methods.

EXAMPLE 5

Determination of OP-1 Protein Production

Where OP-1 acts as the reporter gene, detection of the gene product readily can be assayed using antibodies specific to the protein and standard immunoassay testings. For example, OP-1 may be detected using a polyclonal antibody specific for OP-1 in an ELISA, as follows.

1 $\mu$g/100 $\mu$l of affinity-purified polyclonal rabbit IgG specific for OP-1 is added to each well of a 96-well plate and incubated at 37° C. for an hour. The wells are washed four times with 0.167M sodium borate buffer with 0.15 M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 $\mu$l aliquot of an appropriate dilution of each of the test samples of cell culture supernatant is added to each well in triplicate and incubated at 37° C. for 30 min. After incubation, 100 ll biotinylated rabbit anti-OP-1 serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 μl streptavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 μl substrate (ELISA Amplification System Kit, Life Technologies, Inc., Bethesda, Md.) is added to each well incubated at room temperature for 15 min. Then, 50 μl amplifier (from the same amplification system kit) is added and incubated for another 15 min. at room temperature. The reaction is stopped by the addition of 50 μl 0.3 M sulfuric acid. The OD at 490 nm of the solution in each well is recorded. To quantitate OP-1 in culture media, a OP-1 standard curve is performed in parallel with the test samples.

EXAMPLE 6

Production of OP-1 Polyclonal and Monoclonal Antibodies

Polyclonal antibody for OP-1 protein may be prepared as follows. Each rabbit is given a primary immunization of 100 μg/500 μl E. coli produced OP-1 monomer (amino acids 328–431 in SEQ ID No:5) in 0.1% SDS mixed with 500 μl Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP-1 is detected in the serum using an ELISA assay. Then, the rabbit is boosted monthly with 100 μg of antigen and bled (15 ml per bleed) at days seven and ten after boosting.

Monoclonal antibody specific for OP-1 protein may be prepared as follows. A mouse is given two injections of E. coli produced OP-1 monomer. The first injection contains 100 μg of OP-1 in complete Freund's adjuvant and is given subcutaneously. The second injection contains 50 μg of OP-1 in incomplete adjuvant and is given intraperitoneally. The mouse then receives a total of 230 μg of OP-1 in four intraperitoneal injections at various times over an eight month period. One week prior to fusion, both mice are boosted intraperitoneally with 100 μg of OP-1 and 30 μg of the N-terminal peptide ($Ser_{293}$-$Asn_{309}$-Cys) conjugated through the added cysteine to bovine serum albumin with SMCC crosslinking agent. This boost was repeated five days (IP), four days (IP), three days (IP) and one day (IV) prior to fusion. The mouse spleen cells are then fused to myeloma cells at a ratio of 1:1 using PEG 1500 (Boeringer Mannheim), and the cell fusion is plated and screened for OP-1-specific antibodies using OP-1 as antigen. The cell fusion and monoclonal screening are then performed according to standard procedures widely available in the art.

EXAMPLE 7

Process for Detecting OP-1 in Serum

Presented below is a sample protocol for identifying OP-1 in serum. Following this general methodology, OP-1 may be detected in body fluids, including serum, and can be used in a protocol for evaluating the efficacy of an OP-1 modulating compound in vivo.

A monoclonal antibody raised against mammalian, recombinantly produced OP-1 using standard immunology techniques well described in the art and described generally in example 6, above, was immobilized by passing the antibody over an agarose-activated gel (e.g., Affi-Gel™, from Bio-Rad Laboratories, Richmond, Calif., prepared following manufacturer's instructions) and used to purify OP-1 from serum. Human serum then was passed over the column and eluted with 3M K-thiocyanate. K-thiocyanate fractions then were dialyzed in 6M urea, 20 mM $PO_4$, pH 7.0, applied to a C8 HPLC column, and eluted with a 20 minute, 25–50% acetonitrile/0.1% TFA gradient Mature, recombinantly produced OP-1 homodimers elute between 20–22 minutes, and are used as a positive control. Fractions then were collected and tested for the presence of OP-1 by standard immunoblot using an OP-1 specific antibody. Using this method OP-1 readily was detected in human serum. See also, PCT/US92/07432 for a detailed description of the assay.

EXAMPLE 8

Considerations for Formulation and Methods for Administering Therapeutic Agents Where the OP-1-modulating agent identified herein comprises part of a tissue or organ preservation solution, any commercially available preservation solution may be used. For example, useful solutions known in the art include Collins solution, Wisconsin solution, Belzer solution, Eurocollins solution and lactated Ringer's solution. Generally, an organ preservation solution usually possesses one or more of the following properties: (a) an osmotic pressure substantially equal to that of the inside of a mammalian cell, (solutions typically are hyperosmolar and have K+ and/or Mg++ ions present in an amount sufficient to produce an osmotic pressure slightly higher than the inside of a mammalian cell); (b) the solution typically is capable of maintaining substantially normal ATP levels in the cells; and (c) the solution usually allows optimum maintenance of glucose metabolism in the cells. Organ preservation solutions also may contain anticoagulants, energy sources such as glucose, fructose and other sugars, metabolites, heavy metal chelators, glycerol and other materials of high viscosity to enhance survival at low temperatures, free oxygen radical inhibiting agents and a pH indicator. A detailed description of preservation solutions and useful components may be found, for example, in U.S. Pat. No. 5,002,965.

Where the OP-1-modulating agent is to be provided to an individual, e.g., the donor prior to harvest, or the recipient prior to or concomitant with transplantation, the therapeutic agent may be provided by any suitable means, preferably directly (e.g., locally, as by injection to the tissue or organ locus) or systemically (e.g., parenterally or orally).

Useful solutions for parenteral administration may be prepared by any of the methods well known in the pharmaceutical art, described, for example, in *Remington's Pharmaceutical Sciences* (Gennaro, A., ed.), Mack Pub., 1990. Formulations may include, for example, polyalkylene glycols such as polyethylene glycol, oils of vegetable original, hydrogenated naphthalenes, and the like. Formulations for direct administration, in particular, may include glycerol and other compositions of high viscosity to help maintain the agent at the desired locus. Biocompatible, preferably bioresorbable, polymers, including, for example, hyaluronic acid, collagen, tricalcium phosphate, polybutyrate, lactide and glycolide polymers and lactide/glycolide copolymers, may be useful excipients to control the release of the agent in vivo.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. Where the morphogen-stimulating agent is part of a preservation solution, the dosage likely will depend for example, on the size of the tissue or organ to be transplanted, the overall health status of the organ or tissue itself, the length of time between harvest and transplantation (e.g., the duration in storage), the frequency with which the preservation solution is changed, and the type of storage anticipated, e.g., low temperature. In general terms, preferred ranges include a concentration range between about 0.1 ng to 100 µg/kg per tissue or organ weight per day.

Where the therapeutic agent is to be administered to a donor or recipient, the preferred dosage of drug to be administered also is likely to depend on such variables as the type and extent of progression of the disease, the overall health status of the particular patient, the relative biological efficacy of the compound selected, the formulation of the compound excipients, and its route of administration. In general terms, a suitable compound of this invention may be provided in an aqueous physiological buffer solution containing about 0.001% to 10% w/v compound for parenteral administration. Typical dose ranges are from about 10 ng/kg to about 1 g/kg of body weight per day; and preferred dose range is from about 0.1 µg/kg to 100 mg/kg of body weight per day.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

EXAMPLE 9

Figure 2:
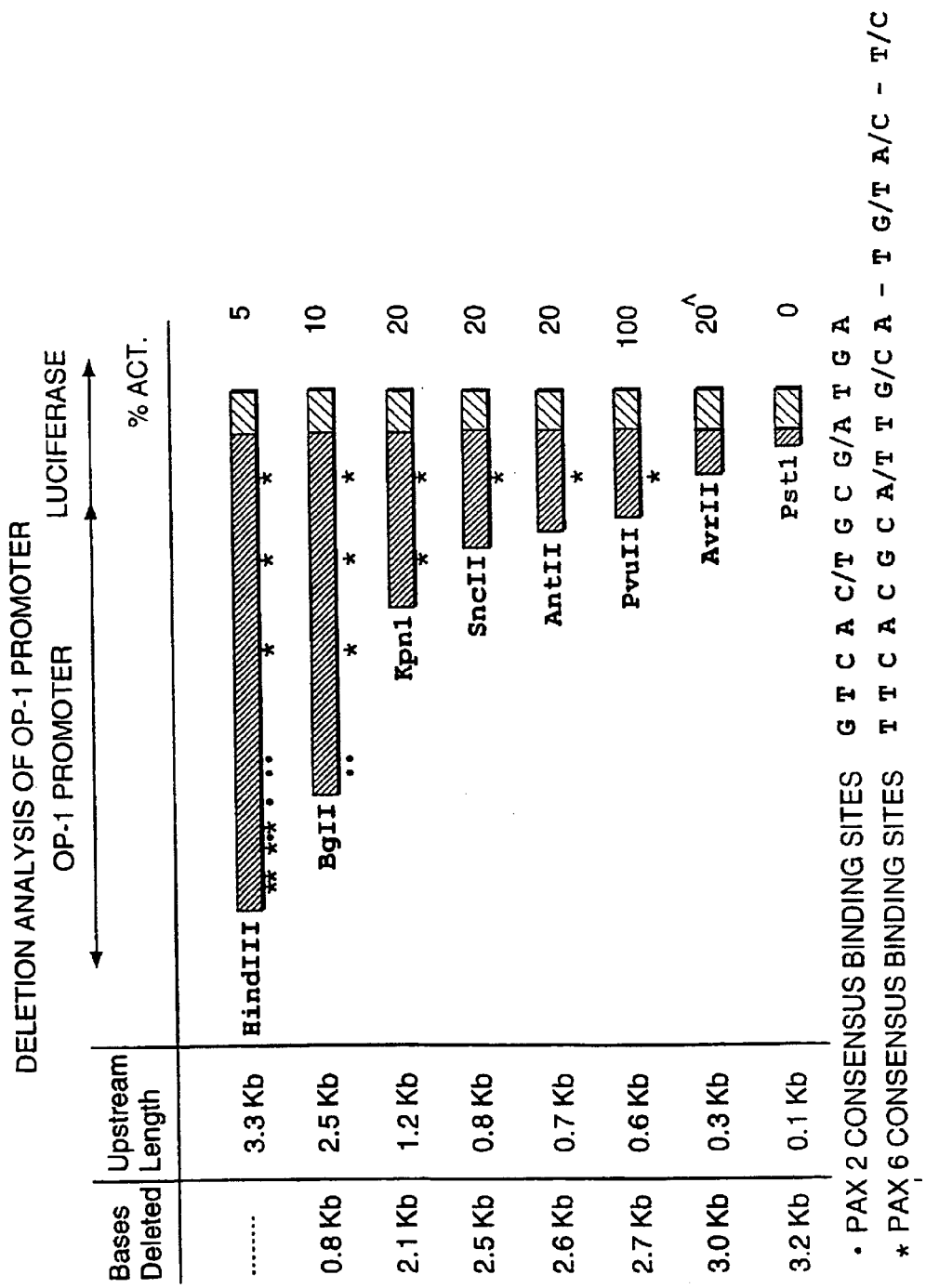
FIG. 2 (SEQ ID NOS: 2–3) shows the relative levels of luciferase expression from constructs containing 5' non-coding regions of the OP-1 gene in operative association with a luciferase reporter gene.

An AatII-PvuII Fragment of the OP-1 Upstream Region Contains an Expression Silencer Luciferase levels were assayed in G401 cells transfected with the OP-1 upstream deletion constructs described in Example 2. The G401 cells were transfected with the deletion constructs using Lipofectamine. Forty-eight to seventy-two hours later, luciferase activity was measured using the Promega Luciferase Assay System (Promega, Madison Wis.) and a luminometer (DynaTech). The relative luciferase activities are shown in FIG. 2. Maximal activity was observed for the construct containing 0.6 kb of OP-1 upstream DNA. The addition of approximately 0.1 kb of upstream DNA (the AatII-PvuII fragment, approximately nucleotides 2606–2690 of SEQ ID NO: 1) reduces luciferase activity approximately five fold as shown in FIG. 2 by the AatII construct containing approximately 0.7 kb of OP-1 upstream DNA.

The expression silencing property of the AatII-PvuII fragment (nucleotides 2606–2690 of SEQ ID NO: 1) was further tested by comparing luciferase expression in pAS33 containing cells with luciferase expression in pAS3.3d containing cells. The pAS3.3 construct contains 3.3 kb of OP-1 upstream DNA fused to the luciferase gene. The pAS3.3d construct lacks the AatII-PvuII fragment, and was made by digesting the pAS3.3 construct with AatII and PvuII, blunting the AatII overhang, and religating the vector.

Figure 3:
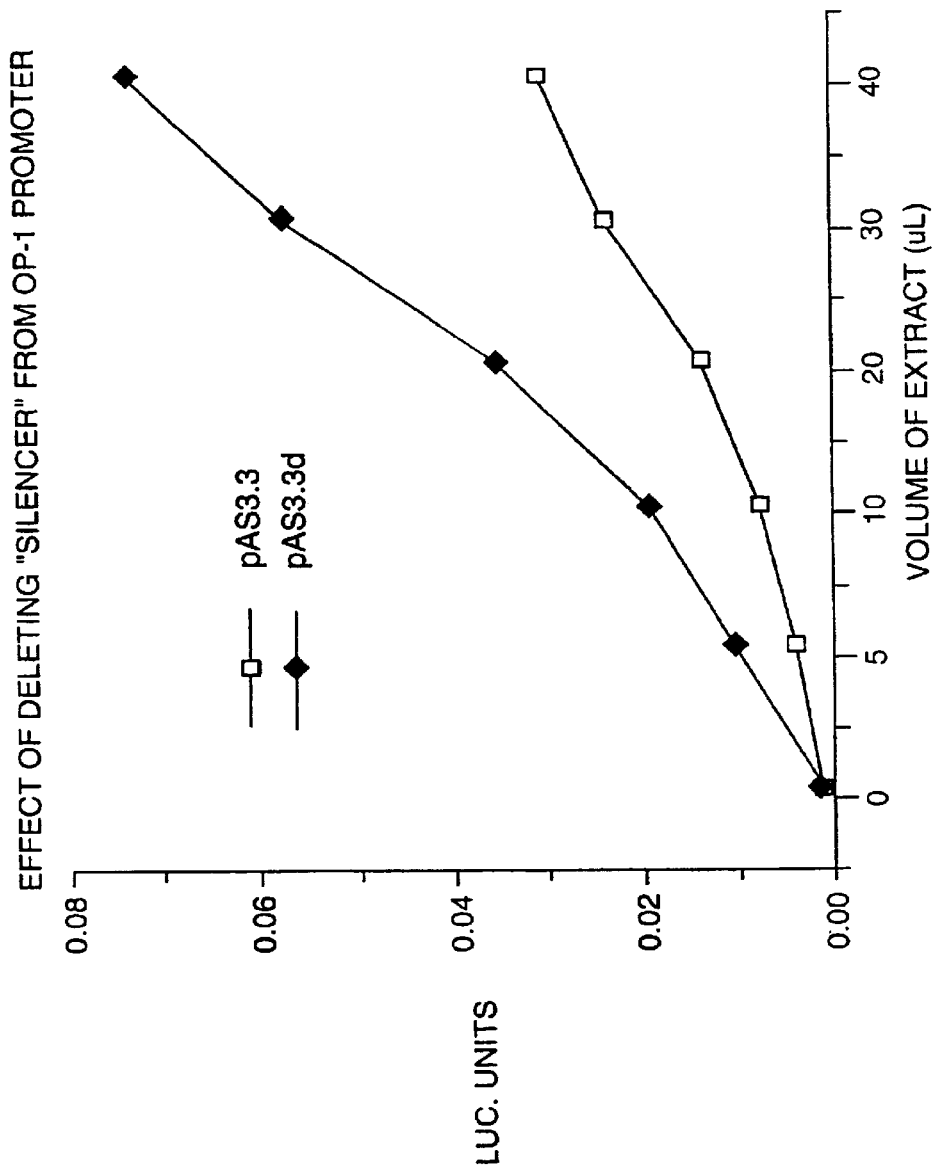
FIG. 3 shows the levels of luciferase expression in cells containing pAS3.3 and pAS3.3d.

G401 cells were plated in triplicate in 6 well plates. After a one day incubation, the cultured cells were transfected with the deletion constructs, using Lipofectamine and approximately 1 µg of either pAS3.3 or pAS3.3d. Forty-eight to seventy-two hours later, luciferase activity was measured as described previously. The results are shown in FIG. 3. Cells containing pAS3.3 expressed approximately three-fold (between two and four-fold) more luciferase than cells containing pAS3.3d. The AatII-PvuII fragment (nucleotides 2606–2690 of SEQ ID NO: 1) therefore contains a silencer of gene expression.

The luciferase production by cells containing the pAS3.3 construct, comprising 3305 nucleotides upstream of the translation start site of the OP-1 gene, was induced 2.4 fold by co-transfection with the Pax 2 cDNA and 9.6 fold by co-transfection with the Pax 6 cDNA (FIG. 1B). The triple transfection of both the Pax 2 and Pax 6 expression vectors with the pAS3.3 construct resulted in an additive 11.5 fold induction suggesting that Pax 2 and Pax 6 gene products have an additive effect on OP-1 gene expression. Cells containing the 5' deletion mutants of the pAS3.3 construct were less responsive to the inductive effect of co-transfection with Pax 2 or Pax 6 constructs. For example, the pAS2.5 construct was only induced 1.7 fold by co-transfection with the Pax 2 construct and this Pax 2 responsiveness was abolished by further deletion of about 1.3 kb of 5' sequence, with no Pax 2 induction detected for the pAS1.2 construct or the remaining constructs with further 5' deletions.

---

What is claimed is:

1. A method for identifying a candidate compound for the ability to modulate expression of OP-1, said method comprising the steps of:
   (a) incubating a candidate compound with a cell co-transfected with vectors comprising:
      (i) a DNA sequence encoding a reporter gene in operative association with at least one OP-1-specific non-coding sequence which can modulate expression of said reporter gene, wherein said non-coding sequence comprises a first Pax-responsive OP-1 modulating element which is responsive to a first Pax gene expression product; and
      (ii) a DNA sequence encoding a first Pax gene expression product;
   (b) measuring the level of reporter gene expressed in said cell; and
   (c) comparing said level with that of said reporter gene expressed in said cell in the absence of said candidate compound, wherein a change in reporter gene expression level is indicative of said candidate's ability to modulate OP-1 expression.

2. The method of claim 1 wherein in step (a)(i) the DNA sequence encoding the reporter gene is further in association with a second Pax responsive OP-1 modulating element, and wherein in step (a) the cell has also been transfected with a DNA sequence encoding a second Pax gene expression product.

3. The method of claim 2 wherein said first Pax responsive OP-1 modulating element is selected from the group of DNA sequences corresponding to bases 108–121, 139–154, 157–167, 365–378, 497–511, 598–613, 1123–1140, 1144–1161, 1285–1297, 1750–1762, 2001–2023, 2365–2378, or 2931–2944 of SEQ. ID No. 1, and wherein said second Pax responsive OP-1 modulating element is selected from the group of DNA sequences corresponding to bases 491–503, 737–747, 891–903, or 994–1006 of SEQ. ID. No. 1.

4. The method of claim 2, wherein said first Pax responsive modulating element is a Pax 6 responsive modulating element and said second Pax responsive modulating element is a Pax 2 responsive modulating element, and wherein said first Pax gene expression product is Pax 6 and said second Pax expression product is Pax 2.

5. The method of claim 1, wherein said first Pax-responsive OP-1 modulating element is a Pax 6-responsive modulating element, and wherein said first Pax gene expression product is Pax 6.

6. The method of claim 5, wherein said Pax 6 responsive modulating element comprises a sequence corresponding to one of the following series of bases of SEQ ID NO:1: 108–121, 139–154, 157–167, 365–378, 497–511, 598–613, 1123–1140, 1144–1161, 1285–1297, 1750–1762, 2001–2023, 2365–2378, or 2931–2944.

7. The method of claim 5, wherein said Pax 6 responsive modulating element comprises SEQ ID NO:2, SEQ ID NO:8 or SEQ ID NO:9.

8. The method of claim 1, wherein said first Pax-responsive OP-1 modulating element is a Pax 2-responsive modulating element, and wherein said first Pax gene expression product is Pax 2.

9. The method of claim 8, wherein said Pax 2-responsive modulating element comprises a sequence corresponding to one of the following series of bases of SEQ ID NO:1: 491–503, 737–747, 891–903, or 994–1006.

10. The method of claim 8, wherein said Pax 2 responsive OP-1 modulating element comprises SEQ ID NO:3, or SEQ ID NO:15.

11. The method of claim 1, wherein said first Pax-responsive OP-1 modulating element comprises a sequence corresponding to one of the following series of bases of SEQ ID NO:1: 1–2073, 1–1297, 1–2691, 1–378, 491–1006, 1750–2023, 1750–2378, 1750–2691, or 1750–2944.

12. An isolated cell transfected with (a) a DNA encoding a reporter gene in operative association with at least one OP-1 specific non-coding sequence, wherein said OP-1 specific non-coding sequence comprises a first Pax-responsive modulating element which is responsive to a first Pax gene expression product and (b) a DNA encoding a first Pax gene expression product.

* * * * *

UNITED STATES PATENT AND TRADEMARK OFFICE
CERTIFICATE OF CORRECTION

PATENT NO. : 6,828,095 B1
DATED : December 7, 2004
INVENTOR(S) : Dorai et al.

It is certified that error appears in the above-identified patent and that said Letters Patent is hereby corrected as shown below:

<u>Title page,</u>
Item [75], Inventors, please replace "Dorai Haimanti" with -- Haimanti Dorai --

Signed and Sealed this

Nineteenth Day of July, 2005

JON W. DUDAS
*Director of the United States Patent and Trademark Office*

SEQUENCE LISTING

<160> NUMBER OF SEQ ID NOS: 15

<210> SEQ ID NO 1
<211> LENGTH: 17415
<212> TYPE: DNA
<213> ORGANISM: Homo sapiens

<400> SEQUENCE: 1

```
tcaaccggtc tctttaggtt ttggctgtgc ttattactat tcattcaaca ggtactaatt      60
gagcacctgc tgtgtgccag gctcagaata ggctcaggtg agatgcacaa agaagggtaa     120
actagaatcc ttgcttagac actgacggat cagttgtttc atatgtaaat tgtagcacca     180
```

```
agacctgctg cccctgcccc cagcctcacc tgcttgtgaa gatccctcca aaagatttga    240
gagtagataa aaagcagaga ctactactga agaacagggc tgctttggct ccttattatt    300
tcagactttg gaagaaaatg acctccttt  tctctactgg cactgagtgc atagctgacc    360
tagcaagcca ggcctggagg gcgtgtgcag ggctgggac cgagcctggt ttctgttccc    420
tgctctgcag ctcaagcact tgctgttcct ccacctggga tgcctttccc tggaaaagcc    480
tgtctctttc ttgtctttca ggactcaggt cagtggcatc cctccaaaa actcccttc     540 ccaccctcca tcacctcacc tgtttatct gcgcccccgc ccccactgcc tgtcacttat    600
tgcaggctga agtgacccag gctctccagt tgtacactct cagatggacc ctggacgact    660
gtggcactcc tgcaatttcc ccagtctccc tggggtagga ttcctgcttg ccaggatgcc    720
cacctttcct tctccctcct gcatgtcctc ctctgcctgg cttctgaatt gtttccagag    780
agagtgatag acaagatctg cctctccttc agtccctgaa tcttatttaa ggctcttgct    840
ttgcttccct ggcctggagg cggctccttg atggagtctg ccatgtgggt tcgctcatgg    900
ccatgtcttc ctgcccagca tggtgcttgg ccctgggact ggccacataa tatctgggcc    960
aggtgcaaaa ttagtacggg gcaggggta ctttgttcat aggtgattca gaaccacata    1020
tggtgacctc agagtaggaa accaagtgtg gggcccttaa gagctggggg gccctgtacg    1080
actgtccagg ttgcaggccc cacagctcgc ctcctgatat cctgtgctcc atgcttgtct    1140
gttgaaggaa ggagtgaatg gatgaagagc aggtggtggg gggtggtttg agggccttgc    1200
tggtgggtgg gtagaggccc ctccctggca tggggctcaa gacctgttcc atcccacagc    1260
ctggggctgt gtgtaaatgg ccaggacctg caggctggca tttttctgct ccttgcctgg    1320
ctctggctcc cctttctcca cccatgtggc ccctcaggct gccatctagt ccaaaagtcc    1380
caagggagac ccagaggcca cttggcaaac tacttctgct ccagaaaact gtagaagacc    1440
ataattctct tccccagctc tcctgctcca ggaaggacag ccccaaagtg aggcttagca    1500
gagcccctcc cagacaagcg cccccgcttc cccaacctca gcccttccca gttcatccca    1560
aaggccctct ggggacccac tctctcaccc agccccagga gggaaggaga caggatgaac    1620 ttttacccccg ctgccctcac tgccactctg ggtgcagtaa ttcccttgag atcccacacc    1680
ggcagaggga ccgtgtgggtt ctgagtggtc tggggactcc ctgtgacagc gtgcatggct    1740
cggtattgat tgagggatga atggatgagg agagacagga gaggaggccg atggggaggt    1800
ctcaggcaca gacccttgga ggggaagagg atgtgaagac cagcggctgg ctccccaggc    1860
actgccacga ggagggctga tgggaagccc tagtggtggg gctggggtgt ctggtctcag    1920
gctgaggggt ggctggaaag atacagggcc ccgaagagga ggaggtggga agaaccccc    1980 cagctcacac gcagttcact tattcactca acaaatcgtg actgcgcacg tacagtggct    2040
accaggcgct gggttcaagg cactgcgggt accagaggtg cggagaagat cgctgatccg    2100
ggccccagtg ctctgggtgt ctagcggggg taagaaggca ataaagaagg cacggagtaa    2160
ctcaaacagc aattccagac agcaagagaa actacaggaa agaaaacaaa cgtgcgaggg    2220
gcgaggcgag gaaacaacct cagcttgca ggtcttggga gtctctggga ggagaaagca    2280
gcgtctgatg ggggcgggag gtggtgagtg gggagaggtc caggcggagg gaatggcgag    2340
cgagagacag gctggcaacg gcttcaggga ggcgcggagg ggtcagcgtg gctggcttaa    2400
aaggatacat gggactaggg gcaagaccgg ctcaaggtca ccgcttccag gaccttctat    2460
ttccgcgcca cctccgcgct cccccaactt ttcccaccgc ggtccgcagc ccacccgtcc    2520
tgctcgggcc gccttcctgg tccggaccgc gagtgccgag agggcagggc cggctccgat    2580
```

-continued

```
tcctccagcc gcatccccgc gacgtcccgc caggctctag gcaccccgtg ggcactcagt    2640
aaacatttgt cgagcgctct agagggaatg aatgaaccca ctgggcacag ctgggggag    2700 ggcggggccg agggcaggtg ggaggccgcc ggcgcgggag gggcccctcg aagcccgtcc    2760
tcctcctcct cctcctccgc ccaggcccca gcgcgtacca ctctggcgct cccgaggcgg    2820
cctcttgtgc gatccagggc gcacaaggct gggagagcgc cccggggccc ctgctatccg    2880
cgccggaggt tggaagaggg tgggttgccg ccgcccgagg gcgagagcgc cagaggagcg    2940
ggaagaagga gcgctcgccc gcccgcctgc ctcctcgctg cctccccggc gttggctctc    3000
tggactccta ggcttgctgg ctgctcctcc cacccgcgcc cgcctcctca ctcgccttt    3060 cgttcgccgg ggctgctttc caagcccgtc ggtgcgcccg ggcgagtgcg gggcgagggg    3120
cccggggcca gcaccgagca ggggggcggg gtccgggcag agcgcggccg gccggggagg    3180
ggccatgtct ggcgcgggcg cagcggggcc cgtctgcagc aagtgaccga gcggcgcgac    3240
ggccgcctgc ccctctgcc acctggggcg gtgcgggccc ggagcccgga gcccgggtag    3300
cgcgtagagc cggcgcgatg cacgtgcgct cactgcgagc tgcggcgccg cacagcttcg    3360
tggcgctctg ggcaccctg ttcctgctgc gctccgccct ggccgacttc agcctggaca    3420
acgaggtgca ctcgagcttc atccaccggc gcctccgcag ccaggagcgg cgggagatgc    3480
agcgcgagat cctctccatt ttgggcttgc cccaccgccc gcgcccgcac ctccagggca    3540
agcacaactc ggcacccatg ttcatgctgg acctgtacaa cgccatggcg gtggaggagg    3600
gcggcgggcc cggcggccag ggcttctcct accctacaa ggccgtcttc agtacccagg    3660
gcccccctct ggccagcctg caagatagcc atttcctcac cgacgccgac atggtcatga    3720
gcttcgtcaa cctcggtgag taagggcagg cgagggtacg ccgtctcctt tcgggggcac    3780
tttgagactg ggagggaggg agccgcttct tctatgcagc ccgcccagct ttccgctcct    3840
ggctgaaatc gcagtgcctg cccgagggtc tcccacccac agcccatga ctcccaagct    3900 gtgtgcgccc ccaggtcggg ccgctgggtc ggtgagcctg taggggttac tgggaaggag    3960
ggatcctccg aagtcccctc catgttacgc gccggccgc atctctgggg ctggaggcaa    4020
gggcgttcaa agcgcgggc tcggtcatgt gagctgtccc gggccggcgc cggtccgtga    4080
cctggatgta aagggccctt ccggcgagg ctgccttgcc gcccttcctg ggcccctctc    4140
agccctgcct ggctctggca tcgcggccgt cgcacccct taccctccct gtcaagccct    4200
acctgtcccc tcgtggtgcg cccgccttag gctaccggcc gctccgagcc ttggggcccc    4260
tctccgggcg ccgatgcccc attctctctt ggctggagct ggggaagaaa cggtgccatt    4320
gctaattttc tttgttttct ttctttgttt atttttttct ttttcttt tttttctttt    4380 cttttcttt cttttttt ttttttgaga cggagtttca ctcttgctcg cccagactgg    4440
agtgcaatgg cgcgatctct gctcaccgca acctctgcct cccgggttca agcgattctc    4500
gtgcctcagc ctcccgagta gctgggatta caggcatgcg caccatgcct ggctaatttt    4560 gtatttagt agagacaggg tttctccatg ttaggcaggc tggtctcgaa ctcccgatct    4620
caggtgatcc tcccgcctca gcctcccaaa gtggtgctgg gattacaggc gtgaagctgt    4680
gccctgccgc tagtcttcta ttttaagtat ttagtggtag gtcccgggcc ggcagaatct    4740
attttcagca tttaccacgt gtggcgcgca aaccacaggt tttggcgatt gggttgcgcg    4800
ggatctcaga gctgacgacc gcggggggcct ggggtcccg gtttcgact ggagccgcga    4860 cgaccccggc gacggcagcc tggggctgca gccgagggcc ggggagctcc ccctccatat    4920
```

```
gtgcgcgcac attctccaga cttgctcaaa ctaaccccc ggagcagcgc acgggctggg    4980
actgatgatc aaatatttgg tttccgagat aacacacccc gatagcgctg tttcctgagc    5040
cgctttcatt ctacttgtgt aacttgctgc gaaaacccga accaagtcaa gacagcaaac    5100
tcacgcccac gggcctgtgt caacatggaa ataatgatac tgaagcccca cgctgggcac    5160
ctggggcgtg gactggggc gcggggggaag cgcagatccg ccttcatgct tcccctcctc    5220
ctgataaggt ccctggagtt cccggagcc attgtctgta cttaataata actaaatcca    5280
actagtgaac caagcttcag cgaggcaagg ggagggaggt ttagatgcca aaattacctt    5340
caaaaaagtt taaattatac taagcagcca gttaagaagg aagcagcaat atatgacctg    5400
atttagaacc atctccaaga tgtatgaggt ggaaagaagc aaggtgcaga tgagtgggct    5460
gcatgtgtgc ttgtatatca tcgtgtcctc ctggaggaag acaccaggaa ctggagagag    5520
atttttactgg aggggtatat ggcgggggca tagctgggc ttacggagtg ggaggtgggg    5580
tctgattttt cgtcgtctgc acttctgtat ttgtgatttt tttaaaacaa tgtgtattta    5640
ttaactatac caaaaaataa aggaaaattc caaatacata catataaata atgaaccgca    5700
gagctctgtc gccctcctga agcctgggt tagccaggc ctttctctg gtgggggatt     5760
tatagcatct tcccttctgt tgggtacccc ggactccac tgaatgtgca ggtcccagtg    5820
gctgccttca gagcctggct ggaatcatta aaaaggtatt tgtaatctct ggcttctgca    5880
gaaggccctg caaaccaaga gcaaaaaagc ccccagtgct tatgggccgg cagtgtgggc    5940
taggcccggg gctccctgtc cccaagagaa agaccaggtt gctcggaggg tgcctctggg    6000
aactttggtg cgggctattt gctccccca tggcggcagg agcaagctgg gacttgtttg    6060
ggaaggccac agctgggtgg ttttcctcct ctggctgtac atacaccttt caatccattt    6120
ctttcatctt gaaaggacaa agaccggctt gtctgagcct cttaatcagt caggctggct    6180
ttgggctttg gggaccctga ctttctcagg tctagctttc tgggacatca ctccaaatta    6240
gatggcagag tggcttttaa cagagcgcac tgaccttgtt ttctttctct ctctgtccct    6300
aaactcgagg tcattagtta ggtgaagacc tgggctgcag tttggcgaga cacttcctgt    6360
agatgcttct aatgttggcc tttaatttct gctaagcagc agcacacaaa taaatggcct    6420
gtcccttcta tcctgttgta gcttggaatt tctccatagg agggacttgg gggtggcagt    6480
agggttggag agggttgggg ggaggtgtag gagacttgtc tggccactga gtttgctgag    6540
aaagtactgc tatagtgttt ttccttggat tgcaaatcat gttgatctga actgctgatt    6600
tgaagtggat tgagaggatg gaacaataga aggaggatat ggctcaggac agtcaagtac    6660
tggaagaggg aaaggtacaa agaggtgttg gcactgaatg accctgaaca gggctgccct    6720
ggaaatatca gaggtgagtg acaaagagaa ctctagtcga aggtctggaa gtcaattatt    6780
gtctccagct tttgtcccac cctaagggat ggagcatgaa cttcatgcat gtaacatccc    6840
tccaggagcg ctgaggttct gggaattccc agtgctggct accatgccat tcttttctca    6900
ttcactcaag agcgtattgg gatatgcgtg catgaaagca atgtaattat gggcacaacc    6960
tcaaaacctg ctctaatttt tttttttttt ggagatggag tctcgctcca tcacccaggc    7020
tggagtgcaa tggcgcgatc tcagctcact gcaagctcag acctccaggg ttcacaccat    7080
tctcctgcct cagcctcccg agtagctggg aatacaggcg cccgcaccat gcgcggctaa    7140
ttttttttgta ttttttagtag agacggggtt tcactgtgtt agccaggatg gtctcgatct    7200
cctgacctcg tgatccaccc gcctcggcct cccaaagttc tgggattaca ggcgtgacag    7260
ccgtgcccgg aatctgctct aatttttttaa agatatcatt tgcaaacttt gggcacttga    7320
```

-continued

```
gtcactcagt aagatattat ttacaacccc accatagatt caaacctctg tcctagaatg    7380
ttgtcgagtt aggcatctgg cttgcagcaa cagctggctt tcctgtctat gctgtctcct    7440
tccagggagg atgtttcacc cttcatattg aggaaatggg cacagagaac ccatttctct    7500
tactcatcat gtaacttcag tgggatggtc agatctatct ttaacctggc cactcttcca    7560
caagctcaca ctgactccag caagatctta aactagaagg caggagttca aatcctagct    7620
ggtgcagtgg ccaaatctcg gctcacagca ccttctgcct cctgggctca agcgatcctc    7680
tgacctcagt ctcccaagta gctgggacca taggcatgca ccactatgcc tggctaattt    7740
ttgtattttt gtaattttt gtagagacag agtttcacca tgttgcccag cccagtcttg     7800
aactcctgga ctcaagcaat cttcccacct ttgcctacca gagtgccggg attacaggtg    7860
tgagccatca tgctagttgc gcacagttgg gcgaaactga cagatgagaa agcagaacct    7920
cgtgagtcca ctcagtaaga gactccctac tttctttctg agtctttgtt tctcatcaat    7980
tgaatggcaa taaacaactt ggtggcccaa gagttgatga caacagtcct ataagattat    8040
acatgtaaaa gaaacagagt attctacaaa tatcagttat tgatagttca ataggcaacc    8100
tgacattacc ttttcttgga acttgatgaa caactcagaa actcattaat atcaaaccca    8160
atggtgagca cttggtcttt atttatggct gtaagagaag aaattgaatt aactctatgt    8220
aaatgccaac taagaacatc gaagtctgaa atcaacagtt ttcctcgctc atacgacaca    8280
cccaaactca agcagtggtt ccaagcccct ttgaaaaata ccatgggcta acgactttaa    8340
aagcttagaa gtgaattcta cttacttatt acttaaaagt ggttctcaaa cttcaaggtg    8400
aatcaaaatc atctgtagag cttgttaaaa cacaggttgc tggtccaccc caagagtgtc    8460
ttgagtcagt aggtctcaag tagggctcaa gaatatgcat ttctaatgag ctccaggtga    8520
gtctaagtgt tagtcgtcgg tcttgggacc acaactttgg gaacaattga tttagaagaa    8580
ctcaaagatc agaagggggt ggaatatttt taaaattgtg gtaaaatacg cataaacaga    8640
aaaggtacaa ttttaaccac ttagagagag gtgggatcta agaacagaaa ttgttatgcc    8700
atcaaaggtg agttcagata agcattatta aatggtatct atggataaac ttcaggggcc    8760
ctgtggagca acccaatgct gggatgggt ccaggtgtgc tatggtttgg atgtggtttg     8820
tccctacaaa aactcatgtt gaaatttaat tgccagtgta acattattga gaggttatgg    8880
acttttaaga ggcatttggg tcatgaggga tccaccttca gggattagtg cagtctccag    8940
ggagtgagtg agttcccatt ctagtgggac tggattagtt accatacagt ggttgttata    9000
aagtgaggct gcttctggtg ttttatctgt ttgcaggcac ttccttcccc ttccacttct    9060
ctgccaggtt aggatgcagc atgaggccct caccagaagc tgaccagatg tggctgcctg    9120
atcttgaact tcccagtccc cagaaccatg agctaaataa accttttttc tctataaatt    9180
acgcagtcta gagtattcta ttatagcaac acaagacaga ctaagacaca gtggtagaaa    9240
gaacactact gacttctccc atactctggc ctatggacaa gagtgacaga cagacaagag    9300
tgaatatcag ggccctcagg cacattcctc tctgccccct tcctccttct tgcagagtct    9360
ccagtgactg ccagctaatg ctatcataga ccccacctt cccctgactt gattggacca     9420
gaagcagcct cctgatccat ggccaacaat cagattcact ttcaagaatt tgaactaaga    9480
gacactagga agatggccct tgagctgtga gtcctacact tgaaagttct tagcatcttg    9540
gtcaggtacc caccagggcc atgtgcaaac tgagataatg gggacatgga acaagggtaa    9600
gtggagaggg ctggctggag agagacgggc agaggaaagc cctgccaaga ggagcagaga    9660
```

```
tgagagacct tggagggaga ggtaataaaa ggaggcaaag atgattttcc atgcttacaa    9720
ctcacagctg aggcctaact atctttatgt ccataagagg catccttgtg tcgaacctct    9780
cctctttctt gggtcaatgg gggatggttg caagggacca tcagtaggaa ggcatagtac    9840
actaacccag tctggggtgg gcttttagac tagtcttcct cccatgctcc tcctcccatt    9900
ggaaccccgg actttcaaga ctgctaccta gcacaccagt gcaccagatg tcactcaaaa    9960
cctcttcagc aatggcccac tcaccttcaa aaaggctgaa gagcagactg gctgggttct   10020
tcatggtgga ggggcagtct gggaggtttt aaggttgaag atgaaaactt tcacttttgg   10080
ctcaatggtc tgaaaagag aaggaccagc aagtgaactg aagcctcctg gaaagcatct   10140
tgataacagg ggcagagttt caagatgaga agctgtggca cttactctgg ctttggaaat   10200
gacctctaag tatctcagtt aattaaagga gtcaaactct agactcgaag agaagatct   10260 acaattttca ataacatagt ctaccctccc ctccttcccc caccttcacc tcttctttca   10320
tcacaggctt acagggcacc tcttagagcc aggcacggtg ttgggatcag gaacaaggcc   10380
actgctcaca tccagagcct gtgctactta agaagcttcc aggacctctt ggatggctgt   10440
ggttagtgcc ctacttttcc cagcaggttg atgcagaat catgctcttg tcgttcagga   10500
tgaccatggg gaccatgggt ctgagcctgt gaccctccag tctacagtgt gttggtgagg   10560
aaggagcagt tgtcactggg gtcactggca atgggcatgc ctccatctag cttaggcaag   10620
atgcttagac tcagagccag agagtgaaac ccagacacta atgagctgtc ggtgttggtg   10680
tgtgttctct tcctcttcca gtggaacatg acaaggaatt cttccaccca cgctaccacc   10740
atcgagagtt ccggtttgat cttcccaaga tcccagaagg ggaagctgtc acggcagccg   10800
aattccggat ctacaaggac tacatccggg aacgcttcga caatgagacg ttccggatca   10860
gcgtttatca ggtgctccag gagcacttgg gcaggtgggt gctatacggg tatctgggag   10920
aggtgctgag tttcctctgg gggcagagga agaaggtggt gagggtttcc ctcccctccc   10980
accccatgag ctctgcttcc catctgttgg ggtagtggag ctgtgacctg ctaacgcgaa   11040
gcccgtgtct ctcctcctct ctcgcaggga atcggatctc ttcctgctcg acagccgtac   11100
ctctgggcct cggaggaggg ctggctggtg tttgacatca cagccaccag caaccactgg   11160
gtggtcaatc cgcggcacaa cctgggcctg cagctctcgg tggagacgct ggatggtgag   11220
tcccccgcca ctgccagtcc taatgcagcc tgtgctcctg gacttcagga gggtctcagc   11280
agtgctcatg cttgcttcac tacaaacagg cttccccgcc cctcccaacc agtactccat   11340
gttcagcctt ttgatcctgc agccctgtcc cgctcgtggc cctcctgtaa ctgctcttct   11400
gtgcacttgg ctgcttcctg tccagggcag acgatcaacc caagttggc gggcctgatt    11460 gggcggcacg ggcccagaa caagcagccc ttcatggtgg cttcttcaa ggccacggag    11520 gtccacttcc gcagcatccg gtccacgggg agcaaacagc gcagccagaa ccgctccaag   11580
acgcccaaga accaggaagc cctcggatgg ccaacgtggc agggtatctt aggtgggagg   11640
gatcacagac ccaccacagg aacccagcag gccccggcga ccgcaggaga ctgactaaaa   11700
tcattcagtg ctcaccaaga tgctctgagc tctcttcgat tttagcaaac caggagtccg   11760
aagatctaag gagagctggg ggtttgactc cgagagctcg agcagtcccc aagacctggt   11820
cttgactcac gagttagact ccactcagag gctgactgtc tccagggtct acacctctaa   11880
gggcgacact gggctcaagc agactgccgt tttctatatg ggatgagcct tcacagggca   11940
gccagtgggg atgggttgag gtttggctgt agacatcaga aacccaagtc aaatgcgctt   12000
caaccagtag aaaattcacc agcccgcaga gctaaggttg ggtggacatt agggttggtt   12060
```

```
gatccaggag ctcaacagtg tcctctgagc cccagctcct tctgcccac cccaccatct    12120 tcagtgctgc ttcctctcaa ggccacagct gtagttggcc aggggggctt cattatttt    12180 tgctcctggg cagtaggagg aagagaatga atgtctctcc atgggtcttt cttaggaatg    12240
tgggaacttt ttccagaagt ctctatgtct tttagtttgt gttgggtcac ttgcccttcc    12300
tgaaccactt cctgactcct ggacaggatg tgcactgatg agcttagctt tggggatcta    12360
atagtgactt tacaaagcct cttttgagaag gtgacattgg aaccaaggct tgagcagaca    12420
caacaaagat tgcagggagg ggcattgcag gtggaggaaa cggcacatgc aagagccctg    12480
cgtgggagtg agcttggtgt ttggtcaatc agttgtcaga gcacaccggg ccctgtcagc    12540
aggcacagcc tgggcctgct ctgagtatga cagagagccc ctgggaagtt gtaggtggag    12600
gaaagacagg tcatgactag gaaaaaagca atccctctgt tgtgggtgg aaggaaggtt    12660 gcagtgtgtg tgagagagag acaagacaga cagacagaca cttctcaatg tttacaagtg    12720
ctcaggccct gacccgaatg cttccaaatt tacgtagttc tggaaaaccc cctgtatcat    12780
tttcactact caaagaaacc tcgggagtgt tttcttctga aggtcatca ggttttgact    12840 ctctgctgtc tcatttcttc ttgctggtgg tggtgatggt tgcttgtccc aggccctgtc    12900
ccgcatcctc ttgcccctgc agagggatga gtgtgttggg gcctcacgag ttgaggttgt    12960
tcataagcag atctctttga gcagggcgcc tgcagtggcc ttgtgtgagg ctggaggggt    13020
ttcgattccc ttatggaatc caggcagatg tagcatttaa acaacacacg tgtataaaag    13080
aaaccagtgt ccgcagaagg ttccagaaag tattatggga taagactaca tgagagagga    13140
atggggcatt ggcacctccc ttagtagggc ctttgctggg ggtagaaatg agttttaagg    13200
caggttagac cctcgaactg gcttttgaat cgggaaattt accccccagc cgttctgtgc    13260
ttcattgctg ttcacatcac tgcctaagat ggaggaactt tgatgtgtgt gtgtttcttt    13320
ctcctcactg ggctctgctt cttcacttcc ttgtcaatgc agagaacagc agcaggcacc    13380
agaggcaggc cttgtaagaa gcacgagctg tatgtcagct tccgagacct gggctggcag    13440
gtaaggggct ggctgggtct gtcttgggtg tgggccctct ggcgtgggct cccacaggca    13500
gcgggtgctg tgctcagtct tgtttctcat ctctgccagt taagactcca gtatcaagtg    13560
gcctcgctag ggaaggggac ttgggctaag gatacaggga ggcctcatga aatccgagag    13620
cagaaatgtg gttgagactt gaactcgaac caggaaccca aacactttgg actctgaacc    13680
ccattctctg catgcacctc attcccatcc cttggctggc tgcttctcaa gatgatgccg    13740
ggccgtgtgt ttgaatgtag atacctgggg agccatctcc ccctctgccc tctgacttca    13800
tttaccccat tcccattccc acgggaggga cggatctccc cagcttggtt caggcgcttg    13860
ttcctgaacc agtcaactgt ttcaggggtg gggtcatgtt actggcacat ggctgccccc    13920
tctggagcca tttgcatgga gtgaggcaaa aggcagggga tgaatctagg agaggagtga    13980
gggtcatgtg atccacctgc cgtgagctct ggatcgtgat tctcattcag cagtcacgag    14040
catctcgagc gttctgggcc ctgttctagg tactggattg gagatgcagc gatgaacact    14100
gcaatgtgtc tgccctgtgg ggctcaaata tccctggaga gggtattgtc atgaggtcat    14160
cagggcaact ggtggtattc taccctcagg gagcttgtag ttcagtggga gagtccagaa    14220
tcttccctgg ggattatgcc cagacacact cagggcgtac gtgcacacag ccagctctga    14280
gccctcctgt gagcctgccc tcaggactga tgaccacatc tacctgcagc tgggacagaa    14340
cccaaactcc aggggcctct gctggaagat tccatgtgct taagcatcac tgaggagtat    14400
```

```
attgattatt gggcaacatt tctgtgccac ccagaccccta gaggcaagga tggcacatgg   14460
atcccttact gaccagtgca cccggagcca gcatgggtga tgccattatg agttattagc   14520
ctctctggca ggtgggcaaa ccgaggcatg gaggtttgtt taaggtgaac tgccagtgtg   14580
tgaccaccta gtgggggtag agctgatgat tgcctcacac cggaggctcc ttcctgtgcc   14640
gcgttctgtc cagaagacac agccatggat gtccatttta ggatcagcca agcccgtggg   14700
gctttccttc attttttattt tatgttttttt tagaaatggg gtcttgctct gtcacccagg   14760
ctggggtgca gtggtgtgat catacgtcac cgcagctttg agccgtcttc ccactcagtc   14820
tactaagctt ggactatagg ccaagactat agagtggtcc ttctttccat tcttttggga   14880
ccatgagagg ccacccatgt ttcctgcccc tgctgggccc tgctgctcag aaggcatggt   14940
ctgaggcttt caccttggtc gtgagccttc gtggtggttt ctttcagcat ggggtttggga   15000 tgctgtgctc aggcttctgc atggtttccc acactctctt ctcctcctca ggactggatc   15060
atcgcgcctg aaggctacgc gcgctactac tgtgaggggg agtgtgcctt ccctctgaac   15120
tcctacatga acgccaccaa ccacgccatc gtgcagacgc tggtgggtgt cacgccatct   15180
tggggtgtgg tcacctgggc cgggcaggct gcggggccac cagatcctgc tgcctccaag   15240
ctggggcctg agtagatgtc agcccattgc catgtcatga cttttggggg cccttgcgc   15300 cgttaaaaaa aaatcaaaaa ttgtacttta tgactggttt ggtataaaga ggagtataat   15360 cttcgacccct ggagttcatt tatttctcct aatttttaaa gtaactaaaa gttgtatggg   15420
ctcctttgag gatgcttgta gtattgtggg tgctggttac ggtgcctaag agcactgggc   15480
ccctgcttca ttttccagta gaggaaacag gtaaacagat gagaaatttc agtgaggggc   15540
acagtgatca gaagcgggcc agcaggataa tgggatggag agatgagtgg ggacccatgg   15600
gccatttcaa gttaaatttc agtcgggtca ccaggaagat tccatgtgat aatgagatta   15660
acgtgcccag tcacggcgac actcagtagg tgttattcct gctctgccaa cagcaaccat   15720
agttgataag agctgttagg gattttgtcc ttttgcttag aatccaaggt tcaaggacct   15780
tggttatgta gctccctgtc atgaacatca tctgagcctt tcctgcctac tgatcatcca   15840
ccctgccttg aatgcttcta gtgacagaga gctcactacc aggactactc cctcctttca   15900
tttagtaatc tgcctccttc ttttcttgtc cctgtcctgt gtgttaagtc ctggagaaaa   15960
atctcatcta tccctttcat ttgattctgc tctttgaggg caggggtttt tgtttctttg   16020
tttgtttttt taagtgttgg ttttccaaag cccttgctcc cctcctcaat tgaaacttca   16080
aagccctcat tgggattgaa ggtccttagg ctggaaacag aagagtcctc cccaacctgt   16140
tccctggcct ggatgtgctg tgctgtgcca gtatccctg gaaggtgcca ggcatgtctc   16200
cccggctgcc agggggacaca tctctatcct tctccaaccc ctgccttcat ggcccatgga   16260
acaggagtgc catcgccctg tgtgcaccta cttccatcag tatttcacca gagatctgca   16320
ggatcaaagt gaattctcca gggattgtga aatgatgcga ttgtggtcat gtttaaaagg   16380
gggcaactgt cttctagaga gtcctgatga aatgcttcca gaggaaatga gctgatggct   16440
ggaatttgct ttaaaatcat tcaaggtgga gcaggtgggg aagggtatgg atgtgtaaga   16500
gtttgaaatt gtccatcata aaatgtgtaa aaagcatgct ggcctatgtc agcagtcaca   16560
gcctggaggt ggtaacagag tgccagtcac tgatgctcaa gcctggcacc tacagttgct   16620
ggaaacccag aagtttcacg ttgaaaacaa caggacagtg gaatctctgg ccctgtcttg   16680
aacacgtggc agatctgcta acactgatct tggtttggctg ccgtcagctt aggttgagtg   16740
gcggtcttcc cttagtttgc ttagtccccg ctattcccta ttgtcttacc tcggtctatt   16800
```

-continued

```
ttgcttatca gtggacctca cgaggcactc ataggcattt gagtctatgt gtccctgtcc    16860
cacatcctct gtaaggtgca gagaagtcca tgagcaagat ggagcacttc tagtgggtcc    16920
aagtcaggga cactattcag caatctacag tgcacagggc agttccccaa cagagaatta    16980
cctggtcctg aatgtcggat ctggccccctt ccttccccac tgtataatgt gaaaacctct   17040
atgctttgtt ccccttgtct gcaaaacagg gataatccca gaactgagtt gtccatgtaa    17100
agtgcttaga acagggagtg cttggcttgg ggagtgtcac ctgcagtcat tcattatgcc    17160
cagacaggat gtttctttat agaaacgtgg aggccagtta gaacgactca ccgcttctca    17220
ccactgccca tgttttggtg tgtgtttcag gtccacttca tcaacccgga aacggtgccc    17280
aagccctgct gtgcgcccac gcagctcaat gccatctccg tcctctactt cgatgacagc    17340
tccaacgtca tcctgaagaa atacagaaac atggtggtcc gggcctgtgg ctgccactag    17400
ctcctccgag aattc                                                     17415
```

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Consensus
      Sequence
<220> FEATURE:
<221> NAME/KEY: modified_base
<222> LOCATION: (1)..(17)
<223> OTHER INFORMATION: n=a, c, g, or t

<400> SEQUENCE: 2
ttcacgcwts antkmny                                                   17

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Consensus
      Sequence
<220> FEATURE:
<221> NAME/KEY: modified_base
<222> LOCATION: (1)..(11)
<223> OTHER INFORMATION: n=a, c, g, or t

<400> SEQUENCE: 3
gtcaygcrtg a                                                         11

<210> SEQ ID NO 4
<211> LENGTH: 102
<212> TYPE: PRT
<213> ORGANISM: Artificial Sequence
<220> FEATURE:
<223> OTHER INFORMATION: Description of Artificial Sequence: Generic
      sequence OPX
<220> FEATURE:
<221> NAME/KEY: SITE
<222> LOCATION: (2)
<223> OTHER INFORMATION: Xaa=Lys or Arg
<220> FEATURE:
<221> NAME/KEY: SITE
<222> LOCATION: (3)
<223> OTHER INFORMATION: Xaa=Lys or Arg
<220> FEATURE:
<221> NAME/KEY: SITE
<222> LOCATION: (11)
<223> OTHER INFORMATION: Xaa=Arg or Gln
<220> FEATURE:
<221> NAME/KEY: SITE -continued

```
<222> LOCATION: (16)
<223> OTHER INFORMATION: Xaa=Gln or Leu
<220> FEATURE:
<221> NAME/KEY: SITE
<222> LOCATION: (19)
<223> OTHER INFORMATION: Xaa=Ile or Val
<220> FEATURE:
<221> NAME/KEY: SITE
<222> LOCATION: (23)
<223> OTHER INFORMATION: Xaa=Glu or Gln
<220> FEATURE:
<221> NAME/KEY: SITE
<222> LOCATION: (26)
<223> OTHER INFORMATION: Xaa=Ala or Ser
<220> FEATURE:
<221> NAME/KEY: SITE
<222> LOCATION: (35)
<223> OTHER INFORMATION: Xaa=Ala or Ser
<220> FEATURE:
<221> NAME/KEY: SITE
<222> LOCATION: (39)
<223> OTHER INFORMATION: Xaa=Asn or Asp
<220> FEATURE:
<221> NAME/KEY: SITE
<222> LOCATION: (41)
<223> OTHER INFORMATION: Xaa=Tyr or Cys
<220> FEATURE:
<221> NAME/KEY: SITE
<222> LOCATION: (50)
<223> OTHER INFORMATION: Xaa=Val or Leu
<220> FEATURE:
<221> NAME/KEY: SITE
<222> LOCATION: (52)
<223> OTHER INFORMATION: Xaa=Ser or Thr
<220> FEATURE:
<221> NAME/KEY: SITE
<222> LOCATION: (56)
<223> OTHER INFORMATION: Xaa=Phe or Leu
<220> FEATURE:
<221> NAME/KEY: SITE
<222> LOCATION: (57)
<223> OTHER INFORMATION: Xaa=Ile or Met
<220> FEATURE:
<221> NAME/KEY: SITE
<222> LOCATION: (58)
<223> OTHER INFORMATION: Xaa=Asn or Lys
<220> FEATURE:
<221> NAME/KEY: SITE
<222> LOCATION: (60)
<223> OTHER INFORMATION: Xaa=Gln, Asp or Asn
<220> FEATURE:
<221> NAME/KEY: SITE
<222> LOCATION: (61)
<223> OTHER INFORMATION: Xaa=Thr, Ala or Val
<220> FEATURE:
<221> NAME/KEY: SITE
<222> LOCATION: (65)
<223> OTHER INFORMATION: Xaa=Pro or Ala
<220> FEATURE:
<221> NAME/KEY: SITE
<222> LOCATION: (71)
<223> OTHER INFORMATION: Xaa=Gln or Lys
<220> FEATURE:
<221> NAME/KEY: SITE
<222> LOCATION: (73)
<223> OTHER INFORMATION: Xaa=Asn or Ser
<220> FEATURE:
<221> NAME/KEY: SITE
<222> LOCATION: (75)
<223> OTHER INFORMATION: Xaa=Ile or Thr
<220> FEATURE:
<221> NAME/KEY: SITE
<222> LOCATION: (80)
<223> OTHER INFORMATION: Xaa=Phe or Tyr
<220> FEATURE:
<221> NAME/KEY: SITE
<222> LOCATION: (82)
<223> OTHER INFORMATION: Xaa=Asp or Ser
<220> FEATURE:
```

-continued

<221> NAME/KEY: SITE
<222> LOCATION: (84)
<223> OTHER INFORMATION: Xaa=Ser or Asn
<220> FEATURE:
<221> NAME/KEY: SITE
<222> LOCATION: (89)
<223> OTHER INFORMATION: Xaa=Lys or Arg
<220> FEATURE:
<221> NAME/KEY: SITE
<222> LOCATION: (91)
<223> OTHER INFORMATION: Xaa=Tyr or His
<220> FEATURE:
<221> NAME/KEY: SITE
<222> LOCATION: (97)
<223> OTHER INFORMATION: Xaa=Arg or Lys

<400> SEQUENCE: 4

```
Cys Xaa Xaa His Glu Leu Tyr Val Ser Phe Xaa Asp Leu Gly Trp Xaa
  1               5                  10                  15

Asp Trp Xaa Ile Ala Pro Xaa Gly Tyr Xaa Ala Tyr Tyr Cys Glu Gly
             20                  25                  30

Glu Cys Xaa Phe Pro Leu Xaa Ser Xaa Met Asn Ala Thr Asn His Ala
         35                  40                  45

Ile Xaa Gln Xaa Leu Val His Xaa Xaa Xaa Pro Xaa Xaa Val Pro Lys
     50                  55                  60

Xaa Cys Cys Ala Pro Thr Xaa Leu Xaa Ala Xaa Ser Val Leu Tyr Xaa
 65                  70                  75                  80

Asp Xaa Ser Xaa Asn Val Ile Leu Xaa Lys Xaa Arg Asn Met Val Val
                 85                  90                  95

Xaa Ala Cys Gly Cys His
            100
```

<210> SEQ ID NO 5
<211> LENGTH: 97
<212> TYPE: PRT
<213> ORGANISM: Artificial Sequence
<220> FEATURE:
<223> OTHER INFORMATION: Description of Artificial Sequence: Generic morphogenic sequence
<220> FEATURE:
<221> NAME/KEY: SITE
<222> LOCATION: (1)
<223> OTHER INFORMATION: Xaa=Phe, Leu or Glu
<220> FEATURE:
<221> NAME/KEY: SITE
<222> LOCATION: (2)
<223> OTHER INFORMATION: Xaa=Tyr, Phe, His, Arg, Thr, Lys, Gln, Val, or Glu
<220> FEATURE:
<221> NAME/KEY: SITE
<222> LOCATION: (3)
<223> OTHER INFORMATION: Xaa=Val, Ile, Leu, or Asp
<220> FEATURE:
<221> NAME/KEY: SITE
<222> LOCATION: (4)
<223> OTHER INFORMATION: Xaa=Ser, Asp, Glu, Asn, or Phe
<220> FEATURE:
<221> NAME/KEY: SITE
<222> LOCATION: (5)
<223> OTHER INFORMATION: Xaa=Phe or Glu
<220> FEATURE:
<221> NAME/KEY: SITE
<222> LOCATION: (6)
<223> OTHER INFORMATION: Xaa=Arg, Gln, Lys, Ser, Glu, Ala, or Asn
<220> FEATURE:
<221> NAME/KEY: SITE
<222> LOCATION: (7)
<223> OTHER INFORMATION: Xaa=Asp, Glu, Leu, Ala, or Gln
<220> FEATURE:
<221> NAME/KEY: SITE
<222> LOCATION: (8)

```
<223> OTHER INFORMATION: Xaa=Leu, Val, Met, Ile, or Phe
<220> FEATURE:
<221> NAME/KEY: SITE
<222> LOCATION: (9)
<223> OTHER INFORMATION: Xaa=Gly, His or Lys
<220> FEATURE:
<221> NAME/KEY: SITE
<222> LOCATION: (10)
<223> OTHER INFORMATION: Xaa=Trp or Met
<220> FEATURE:
<221> NAME/KEY: SITE
<222> LOCATION: (11)
<223> OTHER INFORMATION: Xaa=Gln, Leu, His, Glu, Asn, Asp, Ser, or Gly
<220> FEATURE:
<221> NAME/KEY: SITE
<222> LOCATION: (12)
<223> OTHER INFORMATION: Xaa=Asp, Asn, Ser, Lys, Arg, Glu, or His
<220> FEATURE:
<221> NAME/KEY: SITE
<222> LOCATION: (13)
<223> OTHER INFORMATION: Xaa=Trp or Ser
<220> FEATURE:
<221> NAME/KEY: SITE
<222> LOCATION: (14)
<223> OTHER INFORMATION: Xaa=Ile or Val
<220> FEATURE:
<221> NAME/KEY: SITE
<222> LOCATION: (15)
<223> OTHER INFORMATION: Xaa=Ile or Val
<220> FEATURE:
<221> NAME/KEY: SITE
<222> LOCATION: (16)
<223> OTHER INFORMATION: Xaa=Ala, Ser, Tyr, or Trp
<220> FEATURE:
<221> NAME/KEY: SITE
<222> LOCATION: (18)
<223> OTHER INFORMATION: Xaa=Glu, Lys, Gln, Met, Pro, Leu, Arg, His, or
      Lys
<220> FEATURE:
<221> NAME/KEY: SITE
<222> LOCATION: (19)
<223> OTHER INFORMATION: Xaa=Gly, Glu, Asp, Lys, Ser, Gln, Arg, or Phe
<220> FEATURE:
<221> NAME/KEY: SITE
<222> LOCATION: (20)
<223> OTHER INFORMATION: Xaa=Tyr or Phe
<220> FEATURE:
<221> NAME/KEY: SITE
<222> LOCATION: (21)
<223> OTHER INFORMATION: Xaa=Ala, Ser, Gly, Met, Gln, His, Glu, Asp,
      Leu, Asn, Lys, or Thr
<220> FEATURE:
<221> NAME/KEY: SITE
<222> LOCATION: (22)
<223> OTHER INFORMATION: Xaa=Ala or Pro
<220> FEATURE:
<221> NAME/KEY: SITE
<222> LOCATION: (23)
<223> OTHER INFORMATION: Xaa=Tyr, Phe, Asn, Ala, or Arg
<220> FEATURE:
<221> NAME/KEY: SITE
<222> LOCATION: (24)
<223> OTHER INFORMATION: Xaa=Tyr, His, Glu, Phe, or Arg
<220> FEATURE:
<221> NAME/KEY: SITE
<222> LOCATION: (26)
<223> OTHER INFORMATION: Xaa=Glu, Asp, Ala, Ser, Tyr, His, Lys, Arg,
      Gln, or Gly
<220> FEATURE:
<221> NAME/KEY: SITE
<222> LOCATION: (28)
<223> OTHER INFORMATION: Xaa=Glu, Asp, Leu, Val, Lys, Gly, Thr, Ala, or
      Gln
<220> FEATURE:
<221> NAME/KEY: SITE
<222> LOCATION: (30)
<223> OTHER INFORMATION: Xaa=Ala, Ser, Ile, Asn, Pro, Glu, Asp, Phe,
      Gln, or Leu
<220> FEATURE:
```

```
<221> NAME/KEY: SITE
<222> LOCATION: (31)
<223> OTHER INFORMATION: Xaa=Phe, Tyr, Leu, Asn, Gly, or Arg
<220> FEATURE:
<221> NAME/KEY: SITE
<222> LOCATION: (32)
<223> OTHER INFORMATION: Xaa=Pro, Ser, Ala, Val
<220> FEATURE:
<221> NAME/KEY: SITE
<222> LOCATION: (33)
<223> OTHER INFORMATION: Xaa=Leu, Met, Glu, Phe, or Val
<220> FEATURE:
<221> NAME/KEY: SITE
<222> LOCATION: (34)
<223> OTHER INFORMATION: Xaa=Asn, Asp, Thr, Gly, Ala, Arg, Leu, or Pro
<220> FEATURE:
<221> NAME/KEY: SITE
<222> LOCATION: (35)
<223> OTHER INFORMATION: Xaa=Ser, Ala, Glu, Asp, Thr, Leu, Lys, Gln, or
     His
<220> FEATURE:
<221> NAME/KEY: SITE
<222> LOCATION: (36)
<223> OTHER INFORMATION: Xaa=Tyr, His, Cys, Ile, Arg, Asp, Asn, Lys,
     Ser Glu, or Gly
<220> FEATURE:
<221> NAME/KEY: SITE
<222> LOCATION: (37)
<223> OTHER INFORMATION: Xaa=Met, Leu, Phe, Val, Gly, or Tyr
<220> FEATURE:
<221> NAME/KEY: SITE
<222> LOCATION: (38)
<223> OTHER INFORMATION: Xaa=Asn, Glu, Thr, Pro, Lys, His, Gly, Met,
     Val, or Arg
<220> FEATURE:
<221> NAME/KEY: SITE
<222> LOCATION: (39)
<223> OTHER INFORMATION: Xaa=Ala, Ser, Gly, Pro, or Phe
<220> FEATURE:
<221> NAME/KEY: SITE
<222> LOCATION: (40)
<223> OTHER INFORMATION: Xaa=Thr, Ser, Leu, Pro, His, or Met
<220> FEATURE:
<221> NAME/KEY: SITE
<222> LOCATION: (41)
<223> OTHER INFORMATION: Xaa=Asn, Lys, Val, Thr, or Gln
<220> FEATURE:
<221> NAME/KEY: SITE
<222> LOCATION: (42)
<223> OTHER INFORMATION: Xaa=His, Tyr or Lys
<220> FEATURE:
<221> NAME/KEY: SITE
<222> LOCATION: (43)
<223> OTHER INFORMATION: Xaa=Ala, Thr, Leu, or Tyr
<220> FEATURE:
<221> NAME/KEY: SITE
<222> LOCATION: (44)
<223> OTHER INFORMATION: Xaa=Ile, Thr, Val, Phe, Tyr, Met, or Pro
<220> FEATURE:
<221> NAME/KEY: SITE
<222> LOCATION: (45)
<223> OTHER INFORMATION: Xaa=Val, Leu, Met, Ile, or His
<220> FEATURE:
<221> NAME/KEY: SITE
<222> LOCATION: (46)
<223> OTHER INFORMATION: Xaa=Gln, Arg or Thr
<220> FEATURE:
<221> NAME/KEY: SITE
<222> LOCATION: (47)
<223> OTHER INFORMATION: Xaa=Thr, Ser, Ala, Asn, or His
<220> FEATURE:
<221> NAME/KEY: SITE
<222> LOCATION: (48)
<223> OTHER INFORMATION: Xaa=Leu, Asn or Ile
<220> FEATURE:
<221> NAME/KEY: SITE
<222> LOCATION: (49)
<223> OTHER INFORMATION: Xaa=Val, Met, Leu, Pro, or Ile
<220> FEATURE:
```

-continued

```
<221> NAME/KEY: SITE
<222> LOCATION: (50)
<223> OTHER INFORMATION: Xaa=His, Asn, Arg, Lys, Tyr, or Gln
<220> FEATURE:
<221> NAME/KEY: SITE
<222> LOCATION: (51)
<223> OTHER INFORMATION: Xaa=Phe, Leu, Ser, Asn, Met, Ala, Arg, Glu,
      Gly, or Gln
<220> FEATURE:
<221> NAME/KEY: SITE
<222> LOCATION: (52)
<223> OTHER INFORMATION: Xaa=Ile, Met, Leu, Val, Lys, Gln, Ala, Tyr
<220> FEATURE:
<221> NAME/KEY: SITE
<222> LOCATION: (53)
<223> OTHER INFORMATION: Xaa=Asn, Phe, Lys, Glu, Asp, Ala, Gln, Gly,
      Leu or Val
<220> FEATURE:
<221> NAME/KEY: SITE
<222> LOCATION: (54)
<223> OTHER INFORMATION: Xaa=Pro, Asn, Ser, Val, or Asp
<220> FEATURE:
<221> NAME/KEY: SITE
<222> LOCATION: (55)
<223> OTHER INFORMATION: Xaa=Glu, Asp, Asn, Lys, Arg, Ser, Gly, Thr,
      Gln, Pro, or His
<220> FEATURE:
<221> NAME/KEY: SITE
<222> LOCATION: (56)
<223> OTHER INFORMATION: Xaa=Thr, His, Tyr, Ala, Ile, Lys, Asp, Ser,
      Gly, or Arg
<220> FEATURE:
<221> NAME/KEY: SITE
<222> LOCATION: (57)
<223> OTHER INFORMATION: Xaa=Val, Ile, Thr, Ala, Leu, or Ser
<220> FEATURE:
<221> NAME/KEY: SITE
<222> LOCATION: (58)
<223> OTHER INFORMATION: Xaa=Pro, Gly, Ser, Asp, or Ala
<220> FEATURE:
<221> NAME/KEY: SITE
<222> LOCATION: (59)
<223> OTHER INFORMATION: Xaa=Lys, Leu, Pro, Ala, Ser, Glu, Arg, or Gly
<220> FEATURE:
<221> NAME/KEY: SIMILAR
<222> LOCATION: (60)
<223> OTHER INFORMATION: Xaa=Pro, Ala, Val, Thr, or Ser
<220> FEATURE:
<221> NAME/KEY: SITE
<222> LOCATION: (61)
<223> OTHER INFORMATION: Xaa=Cys, Val or Ser
<220> FEATURE:
<221> NAME/KEY: SITE
<222> LOCATION: (63)
<223> OTHER INFORMATION: Xaa=Ala, Val or Thr
<220> FEATURE:
<221> NAME/KEY: SITE
<222> LOCATION: (65)
<223> OTHER INFORMATION: Xaa=Thr, Ala, Glu, Val, Gly, Asp, or Tyr
<220> FEATURE:
<221> NAME/KEY: SITE
<222> LOCATION: (66)
<223> OTHER INFORMATION: Xaa=Gln, Lys, Glu, Arg, or Val
<220> FEATURE:
<221> NAME/KEY: SITE
<222> LOCATION: (67)
<223> OTHER INFORMATION: Xaa=Leu, Met, Thr, or Tyr
<220> FEATURE:
<221> NAME/KEY: SITE
<222> LOCATION: (68)
<223> OTHER INFORMATION: Xaa=Asn, Ser, Gly, Thr, Asp, Glu, Lys, or Val
<220> FEATURE:
<221> NAME/KEY: SITE
<222> LOCATION: (69)
<223> OTHER INFORMATION: Xaa=Ala, Pro, Gly, or Ser
<220> FEATURE:
<221> NAME/KEY: SITE
<222> LOCATION: (70)
<223> OTHER INFORMATION: Xaa=Ile, Thr, Leu, or Val
```

```
-continued

<220> FEATURE:
<221> NAME/KEY: SITE
<222> LOCATION: (71)
<223> OTHER INFORMATION: Xaa=Ser, Pro, Ala, Thr, Asn, or Gly
<220> FEATURE:
<221> NAME/KEY: SITE
<222> LOCATION: (72)
<223> OTHER INFORMATION: Xaa=Val, Ile, Leu, or Met
<220> FEATURE:
<221> NAME/KEY: SITE
<222> LOCATION: (74)
<223> OTHER INFORMATION: Xaa=Tyr, Phe, Arg, Thr, Tyr, or Met
<220> FEATURE:
<221> NAME/KEY: SITE
<222> LOCATION: (75)
<223> OTHER INFORMATION: Xaa=Phe, Tyr, His, Leu, Ile, Lys, Gln, or Val
<220> FEATURE:
<221> NAME/KEY: SITE
<222> LOCATION: (76)
<223> OTHER INFORMATION: Xaa=Asp, Leu, Asn, or Glu
<220> FEATURE:
<221> NAME/KEY: SITE
<222> LOCATION: (77)
<223> OTHER INFORMATION: Xaa=Asp, Ser, Arg, Asn, Glu, Ala, Lys, Gly, or
      Pro
<220> FEATURE:
<221> NAME/KEY: SITE
<222> LOCATION: (78)
<223> OTHER INFORMATION: Xaa=Ser, Asn, Asp, Tyr, Ala, Gly, Gln, Met,
      Glu, Asn, or Lys
<220> FEATURE:
<221> NAME/KEY: SITE
<222> LOCATION: (79)
<223> OTHER INFORMATION: Xaa=Ser, Asn, Glu, Asp, Val, Lys, Gly, Gln, or
      Arg
<220> FEATURE:
<221> NAME/KEY: SITE
<222> LOCATION: (80)
<223> OTHER INFORMATION: Xaa=Asn, Lys, Thr, Pro, Val, Ile, Arg, Ser, or
      Gln
<220> FEATURE:
<221> NAME/KEY: SITE
<222> LOCATION: (81)
<223> OTHER INFORMATION: Xaa=Val, Ile, Thr, or Ala
<220> FEATURE:
<221> NAME/KEY: SITE
<222> LOCATION: (82)
<223> OTHER INFORMATION: Xaa=Ile, Asn, Val, Leu, Tyr, Asp, or Ala
<220> FEATURE:
<221> NAME/KEY: SITE
<222> LOCATION: (83)
<223> OTHER INFORMATION: Xaa=Leu, Tyr, Lys, or Ile
<220> FEATURE:
<221> NAME/KEY: SITE
<222> LOCATION: (84)
<223> OTHER INFORMATION: Xaa=Lys, Arg, Asn, Tyr, Phe, Thr, Glu, or Gly
<220> FEATURE:
<221> NAME/KEY: SITE
<222> LOCATION: (85)
<223> OTHER INFORMATION: Xaa=Lys, Arg, His, Gln, Asn, Glu, or Val
<220> FEATURE:
<221> NAME/KEY: SITE
<222> LOCATION: (86)
<223> OTHER INFORMATION: Xaa=Tyr, His, Glu, or Ile
<220> FEATURE:
<221> NAME/KEY: SITE
<222> LOCATION: (87)
<223> OTHER INFORMATION: Xaa=Arg, Glu, Gln, Pro, or Lys
<220> FEATURE:
<221> NAME/KEY: SITE
<222> LOCATION: (88)
<223> OTHER INFORMATION: Xaa=Asn, Asp, Ala, Glu, Gly, or Lys
<220> FEATURE:
<221> NAME/KEY: SITE
<222> LOCATION: (89)
<223> OTHER INFORMATION: Xaa=Met or Ala
<220> FEATURE:
<221> NAME/KEY: SITE
<222> LOCATION: (90)
```

```
<223> OTHER INFORMATION: Xaa=Val, Ile, Ala, Thr, Ser, or Lys
<220> FEATURE:
<221> NAME/KEY: SITE
<222> LOCATION: (91)
<223> OTHER INFORMATION: Xaa=Val or Ala
<220> FEATURE:
<221> NAME/KEY: SITE
<222> LOCATION: (92)
<223> OTHER INFORMATION: Xaa=Arg, Lys, Gln, Asp, Glu, Val, Ala, Ser, or
      Thr
<220> FEATURE:
<221> NAME/KEY: SITE
<222> LOCATION: (93)
<223> OTHER INFORMATION: Xaa=Ala, Ser, Glu, Gly, Arg, or Thr
<220> FEATURE:
<221> NAME/KEY: SITE
<222> LOCATION: (95)
<223> OTHER INFORMATION: Xaa=Gly, Ala or Thr
<220> FEATURE:
<221> NAME/KEY: SITE
<222> LOCATION: (97)
<223> OTHER INFORMATION: Xaa=His, Arg, Gly, Leu, or Ser

<400> SEQUENCE: 5

Xaa Xaa Xaa Xaa Xaa Xaa Xaa Xaa Xaa Xaa Xaa Xaa Xaa Xaa Xaa Xaa
 1               5                  10                  15

Pro Xaa Xaa Xaa Xaa Xaa Xaa Xaa Cys Xaa Gly Xaa Cys Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Cys Xaa Pro
    50                  55                  60

Xaa Xaa Xaa Xaa Xaa Xaa Xaa Xaa Leu Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Cys Xaa Cys
            85                  90                  95

Xaa

<210> SEQ ID NO 6
<211> LENGTH: 102
<212> TYPE: PRT
<213> ORGANISM: Artificial Sequence
<220> FEATURE:
<223> OTHER INFORMATION: Description of Artificial Sequence: Generic
      morphogenic sequence
<220> FEATURE:
<221> NAME/KEY: SITE
<222> LOCATION: (2)
<223> OTHER INFORMATION: Xaa=Lys, Arg, Gln, Ser, His, Glu, Ala, or Cys
<220> FEATURE:
<221> NAME/KEY: SITE
<222> LOCATION: (3)
<223> OTHER INFORMATION: Xaa=Lys, Arg, Met, Lys, Thr, Leu, Tyr, or Ala
<220> FEATURE:
<221> NAME/KEY: SITE
<222> LOCATION: (4)
<223> OTHER INFORMATION: Xaa=His, Gln, Arg, Lys, Thr, Leu, Val, Pro, or
      Tyr
<220> FEATURE:
<221> NAME/KEY: SITE
<222> LOCATION: (5)
<223> OTHER INFORMATION: Xaa=Gln, Thr, His, Arg, Pro, Ser. Ala, Tyr,
      Lys, Asp, or Leu
<220> FEATURE:
<221> NAME/KEY: SITE
<222> LOCATION: (6)
<223> OTHER INFORMATION: Xaa=Phe, Leu or Glu
<220> FEATURE:
<221> NAME/KEY: SITE
<222> LOCATION: (7)
<223> OTHER INFORMATION: Xaa=Tyr, Phe, His, Arg, Thr, Lys, Gln, Val, or
```

```
            Glu
<220> FEATURE:
<221> NAME/KEY: SITE
<222> LOCATION: (8)
<223> OTHER INFORMATION: Xaa=Val, Ile, Leu, or Asp
<220> FEATURE:
<221> NAME/KEY: SITE
<222> LOCATION: (9)
<223> OTHER INFORMATION: Xaa=Ser, Asp, Glu, Asn, or Phe
<220> FEATURE:
<221> NAME/KEY: SITE
<222> LOCATION: (10)
<223> OTHER INFORMATION: Xaa=Phe or Glu
<220> FEATURE:
<221> NAME/KEY: SITE
<222> LOCATION: (11)
<223> OTHER INFORMATION: Xaa=Arg, Gln, Lys, Ser, Glu, Ala, or Asn
<220> FEATURE:
<221> NAME/KEY: SITE
<222> LOCATION: (12)
<223> OTHER INFORMATION: Xaa=Asp, Glu, Leu, Ala, or Gln
<220> FEATURE:
<221> NAME/KEY: SITE
<222> LOCATION: (13)
<223> OTHER INFORMATION: Xaa=Leu, Val, Met, Ile, or Phe
<220> FEATURE:
<221> NAME/KEY: SITE
<222> LOCATION: (14)
<223> OTHER INFORMATION: Xaa=Gly, His or Lys
<220> FEATURE:
<221> NAME/KEY: SITE
<222> LOCATION: (15)
<223> OTHER INFORMATION: Xaa=Trp or Met
<220> FEATURE:
<221> NAME/KEY: SITE
<222> LOCATION: (16)
<223> OTHER INFORMATION: Xaa=Gln, Leu, His, Glu, Asn, Asp, Ser, or Gly
<220> FEATURE:
<221> NAME/KEY: SITE
<222> LOCATION: (17)
<223> OTHER INFORMATION: Xaa=Asp, Asn, Ser, Lys, Arg, Glu, or His
<220> FEATURE:
<221> NAME/KEY: SITE
<222> LOCATION: (18)
<223> OTHER INFORMATION: Xaa=Trp or Ser
<220> FEATURE:
<221> NAME/KEY: SITE
<222> LOCATION: (19)
<223> OTHER INFORMATION: Xaa=Ile or Val
<220> FEATURE:
<221> NAME/KEY: SITE
<222> LOCATION: (20)
<223> OTHER INFORMATION: Xaa=Ile or Val
<220> FEATURE:
<221> NAME/KEY: SITE
<222> LOCATION: (21)
<223> OTHER INFORMATION: Xaa=Ala, Ser, Tyr, or Trp
<220> FEATURE:
<221> NAME/KEY: SITE
<222> LOCATION: (23)
<223> OTHER INFORMATION: Xaa=Glu, Lys, Gln, Met, Pro, Leu, Arg, His, or
      Lys
<220> FEATURE:
<221> NAME/KEY: SITE
<222> LOCATION: (24)
<223> OTHER INFORMATION: Xaa=Gly, Glu, Asp, Lys, Ser, Gln, Arg, or Phe
<220> FEATURE:
<221> NAME/KEY: SITE
<222> LOCATION: (25)
<223> OTHER INFORMATION: Xaa=Tyr or Phe
<220> FEATURE:
<221> NAME/KEY: SITE
<222> LOCATION: (26)
<223> OTHER INFORMATION: Xaa=Ala, Ser, Gly, Met, Gln, His, Glu, Asp,
      Leu, Asn, Lys, or Thr
<220> FEATURE:
<221> NAME/KEY: SITE
<222> LOCATION: (27)
<223> OTHER INFORMATION: Xaa=Ala or Pro
```

```
<220> FEATURE:
<221> NAME/KEY: SITE
<222> LOCATION: (28)
<223> OTHER INFORMATION: Xaa=Tyr, Phe, Asn, Ala, or Arg
<220> FEATURE:
<221> NAME/KEY: SITE
<222> LOCATION: (29)
<223> OTHER INFORMATION: Xaa=Tyr, His, Glu, Phe, or Arg
<220> FEATURE:
<221> NAME/KEY: SITE
<222> LOCATION: (31)
<223> OTHER INFORMATION: Xaa=Glu, Asp, Ala, Ser, Tyr, His, Lys, Arg,
      Gln, or Gly
<220> FEATURE:
<221> NAME/KEY: SITE
<222> LOCATION: (33)
<223> OTHER INFORMATION: Xaa=Glu, Asp, Leu, Val, Lys, Gly, Thr, Ala, or
      Gln
<220> FEATURE:
<221> NAME/KEY: SITE
<222> LOCATION: (35)
<223> OTHER INFORMATION: Xaa=Ala, Ser, Ile, Asn, Pro, Glu, Asp, Phe,
      Gln, or Leu
<220> FEATURE:
<221> NAME/KEY: SITE
<222> LOCATION: (36)
<223> OTHER INFORMATION: Xaa=Phe, Tyr, Leu, Asn, Gly, or Arg
<220> FEATURE:
<221> NAME/KEY: SITE
<222> LOCATION: (37)
<223> OTHER INFORMATION: Xaa=Pro, Ser, Ala, Val
<220> FEATURE:
<221> NAME/KEY: SITE
<222> LOCATION: (38)
<223> OTHER INFORMATION: Xaa=Leu, Met, Glu, Phe, or Val
<220> FEATURE:
<221> NAME/KEY: SITE
<222> LOCATION: (39)
<223> OTHER INFORMATION: Xaa=Asn, Asp, Thr, Gly, Ala, Arg, Leu, or Pro
<220> FEATURE:
<221> NAME/KEY: SITE
<222> LOCATION: (40)
<223> OTHER INFORMATION: Xaa=Ser, Ala, Glu, Asp, Thr, Leu, Lys, Gln, or
      His
<220> FEATURE:
<221> NAME/KEY: SITE
<222> LOCATION: (41)
<223> OTHER INFORMATION: Xaa=Tyr, His, Cys, Ile, Arg, Asp, Asn, Lys,
      Ser, Glu, or Gly
<220> FEATURE:
<221> NAME/KEY: SITE
<222> LOCATION: (42)
<223> OTHER INFORMATION: Xaa=Met, Leu, Phe, Val, Gly, or Tyr
<220> FEATURE:
<221> NAME/KEY: SITE
<222> LOCATION: (43)
<223> OTHER INFORMATION: Xaa=Asn, Glu, Thr, Pro, Lys, His, Gly, Met,
      Val, or Arg
<220> FEATURE:
<221> NAME/KEY: SITE
<222> LOCATION: (44)
<223> OTHER INFORMATION: Xaa=Ala, Ser, Gly, Pro, or Phe
<220> FEATURE:
<221> NAME/KEY: SITE
<222> LOCATION: (45)
<223> OTHER INFORMATION: Xaa=Thr, Ser, Leu, Pro, His, or Met
<220> FEATURE:
<221> NAME/KEY: SITE
<222> LOCATION: (46)
<223> OTHER INFORMATION: Xaa=Asn, Lys, Val, Thr, or Gln
<220> FEATURE:
<221> NAME/KEY: SITE
<222> LOCATION: (47)
<223> OTHER INFORMATION: Xaa=His, Tyr or Lys
<220> FEATURE:
<221> NAME/KEY: SITE
<222> LOCATION: (48)
<223> OTHER INFORMATION: Xaa=Ala, Thr, Leu, or Tyr
<220> FEATURE:
```

```
-continued

<221> NAME/KEY: SITE
<222> LOCATION: (49)
<223> OTHER INFORMATION: Xaa=Ile, Thr, Val, Phe, Tyr, Met, or Pro
<220> FEATURE:
<221> NAME/KEY: SITE
<222> LOCATION: (50)
<223> OTHER INFORMATION: Xaa=Val, Leu, Met, Ile, or His
<220> FEATURE:
<221> NAME/KEY: SITE
<222> LOCATION: (51)
<223> OTHER INFORMATION: Xaa=Gln, Arg or Thr
<220> FEATURE:
<221> NAME/KEY: SITE
<222> LOCATION: (52)
<223> OTHER INFORMATION: Xaa=Thr, Ser, Ala, Asn, or His
<220> FEATURE:
<221> NAME/KEY: SITE
<222> LOCATION: (53)
<223> OTHER INFORMATION: Xaa=Leu, Asn or Ile
<220> FEATURE:
<221> NAME/KEY: SITE
<222> LOCATION: (54)
<223> OTHER INFORMATION: Xaa=Val, Met, Leu, Pro, or Ile
<220> FEATURE:
<221> NAME/KEY: SITE
<222> LOCATION: (55)
<223> OTHER INFORMATION: Xaa=His, Asn, Arg, Lys, Tyr, or Gln
<220> FEATURE:
<221> NAME/KEY: SITE
<222> LOCATION: (56)
<223> OTHER INFORMATION: Xaa=Phe, Leu, Ser, Asn, Met, Ala, Arg, Glu,
      Gly, or Gln
<220> FEATURE:
<221> NAME/KEY: SITE
<222> LOCATION: (57)
<223> OTHER INFORMATION: Xaa=Ile, Met, Leu, Val, Lys, Gln, Ala, Tyr
<220> FEATURE:
<221> NAME/KEY: SITE
<222> LOCATION: (58)
<223> OTHER INFORMATION: Xaa=Asn, Phe, Lys, Glu, Asp, Ala, Gln, Gly,
      Leu, or Val
<220> FEATURE:
<221> NAME/KEY: SITE
<222> LOCATION: (59)
<223> OTHER INFORMATION: Xaa=Pro, Asn, Ser, Val, or Asp
<220> FEATURE:
<221> NAME/KEY: SITE
<222> LOCATION: (60)
<223> OTHER INFORMATION: Xaa=Glu, Asp, Asn, Lys, Arg, Ser, Gly, Thr,
      Gln, Pro, or His
<220> FEATURE:
<221> NAME/KEY: SITE
<222> LOCATION: (61)
<223> OTHER INFORMATION: Xaa=Thr, His, Tyr, Ala, Ile, Lys, Asp, Ser,
      Gly, or Arg
<220> FEATURE:
<221> NAME/KEY: SITE
<222> LOCATION: (62)
<223> OTHER INFORMATION: Xaa=Val, Ile, Thr, Ala, Leu, or Ser
<220> FEATURE:
<221> NAME/KEY: SITE
<222> LOCATION: (63)
<223> OTHER INFORMATION: Xaa=Pro, Gly, Ser, Asp, or Ala
<220> FEATURE:
<221> NAME/KEY: SITE
<222> LOCATION: (64)
<223> OTHER INFORMATION: Xaa=Lys, Leu, Pro, Ala, Ser, Glu, Arg, or Gly
<220> FEATURE:
<221> NAME/KEY: SIMILAR
<222> LOCATION: (65)
<223> OTHER INFORMATION: Xaa=Pro, Ala, Val, Thr, or Ser
<220> FEATURE:
<221> NAME/KEY: SITE
<222> LOCATION: (66)
<223> OTHER INFORMATION: Xaa=Cys, Val or Ser
<220> FEATURE:
<221> NAME/KEY: SITE
<222> LOCATION: (68)
<223> OTHER INFORMATION: Xaa=Ala, Val or Thr
```

```
<220> FEATURE:
<221> NAME/KEY: SITE
<222> LOCATION: (70)
<223> OTHER INFORMATION: Xaa=Thr, Ala, Glu, Val, Gly, Asp, or Tyr
<220> FEATURE:
<221> NAME/KEY: SITE
<222> LOCATION: (71)
<223> OTHER INFORMATION: Xaa=Gln, Lys, Glu, Arg, or Val
<220> FEATURE:
<221> NAME/KEY: SITE
<222> LOCATION: (72)
<223> OTHER INFORMATION: Xaa=Leu, Met, Thr, or Tyr
<220> FEATURE:
<221> NAME/KEY: SITE
<222> LOCATION: (73)
<223> OTHER INFORMATION: Xaa=Asn, Ser, Gly, Thr, Asp, Glu, Lys, or Val
<220> FEATURE:
<221> NAME/KEY: SITE
<222> LOCATION: (74)
<223> OTHER INFORMATION: Xaa=Ala, Pro, Gly, or Ser
<220> FEATURE:
<221> NAME/KEY: SITE
<222> LOCATION: (75)
<223> OTHER INFORMATION: Xaa=Ile, Thr, Leu, or Val
<220> FEATURE:
<221> NAME/KEY: SITE
<222> LOCATION: (76)
<223> OTHER INFORMATION: Xaa=Ser, Pro, Ala, Thr, Asn, or Gly
<220> FEATURE:
<221> NAME/KEY: SITE
<222> LOCATION: (77)
<223> OTHER INFORMATION: Xaa=Val, Ile, Leu, or Met
<220> FEATURE:
<221> NAME/KEY: SITE
<222> LOCATION: (79)
<223> OTHER INFORMATION: Xaa=Tyr, Phe, Arg, Thr, Tyr, or Met
<220> FEATURE:
<221> NAME/KEY: SITE
<222> LOCATION: (80)
<223> OTHER INFORMATION: Xaa=Phe, Tyr, His, Leu, Ile, Lys, Gln, or Val
<220> FEATURE:
<221> NAME/KEY: SITE
<222> LOCATION: (81)
<223> OTHER INFORMATION: Xaa=Asp, Leu, Asn, or Glu
<220> FEATURE:
<221> NAME/KEY: SITE
<222> LOCATION: (82)
<223> OTHER INFORMATION: Xaa=Asp, Ser, Arg, Asn, Glu, Ala, Lys, Gly, or
     Pro
<220> FEATURE:
<221> NAME/KEY: SITE
<222> LOCATION: (83)
<223> OTHER INFORMATION: Xaa=Ser, Asn, Asp, Tyr, Ala, Gly, Gln, Met,
     Glu, Asn, or Lys
<220> FEATURE:
<221> NAME/KEY: SITE
<222> LOCATION: (84)
<223> OTHER INFORMATION: Xaa=Ser, Asn, Glu, Asp, Val, Lys, Gly, Gln, or
     Arg
<220> FEATURE:
<221> NAME/KEY: SITE
<222> LOCATION: (85)
<223> OTHER INFORMATION: Xaa=Asn, Lys, Thr, Pro, Val, Ile, Arg, Ser, or
     Gln
<220> FEATURE:
<221> NAME/KEY: SITE
<222> LOCATION: (86)
<223> OTHER INFORMATION: Xaa=Val, Ile, Thr, or Ala
<220> FEATURE:
<221> NAME/KEY: SITE
<222> LOCATION: (87)
<223> OTHER INFORMATION: Xaa=Ile, Asn, Val, Leu, Tyr, Asp, or Ala
<220> FEATURE:
<221> NAME/KEY: SITE
<222> LOCATION: (88)
<223> OTHER INFORMATION: Xaa=Leu, Tyr, Lys, or Ile
<220> FEATURE:
<221> NAME/KEY: SITE
<222> LOCATION: (89)
```

-continued

```
<223> OTHER INFORMATION: Xaa=Lys, Arg, Asn, Tyr, Phe, Thr, Glu, or Gly
<220> FEATURE:
<221> NAME/KEY: SITE
<222> LOCATION: (90)
<223> OTHER INFORMATION: Xaa=Lys, Arg, His, Gln, Asn, Glu, or Val
<220> FEATURE:
<221> NAME/KEY: SITE
<222> LOCATION: (91)
<223> OTHER INFORMATION: Xaa=Tyr, His, Glu, or Ile
<220> FEATURE:
<221> NAME/KEY: SITE
<222> LOCATION: (92)
<223> OTHER INFORMATION: Xaa=Arg, Glu, Gln, Pro, or Lys
<220> FEATURE:
<221> NAME/KEY: SITE
<222> LOCATION: (93)
<223> OTHER INFORMATION: Xaa=Asn, Asp, Ala, Glu, Gly, or Lys
<220> FEATURE:
<221> NAME/KEY: SITE
<222> LOCATION: (94)
<223> OTHER INFORMATION: Xaa=Met or Ala
<220> FEATURE:
<221> NAME/KEY: SITE
<222> LOCATION: (95)
<223> OTHER INFORMATION: Xaa=Val, Ile, Ala, Thr, Ser, or Lys
<220> FEATURE:
<221> NAME/KEY: SITE
<222> LOCATION: (96)
<223> OTHER INFORMATION: Xaa=Val or Ala
<220> FEATURE:
<221> NAME/KEY: SITE
<222> LOCATION: (97)
<223> OTHER INFORMATION: Xaa=Arg, Lys, Gln, Asp, Glu, Val, Ala, Ser, or
      Thr
<220> FEATURE:
<221> NAME/KEY: SITE
<222> LOCATION: (98)
<223> OTHER INFORMATION: Xaa=Ala, Ser, Glu, Gly, Arg, or Thr
<220> FEATURE:
<221> NAME/KEY: SITE
<222> LOCATION: (100)
<223> OTHER INFORMATION: Xaa=Gly, Ala or Thr
<220> FEATURE:
<221> NAME/KEY: SITE
<222> LOCATION: (102)
<223> OTHER INFORMATION: Xaa=His, Arg, Gly, Leu, or Ser

<400> SEQUENCE: 6

Cys Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Pro Xaa Xaa Xaa Xaa Xaa Xaa Cys Xaa Gly
             20                  25                  30

Xaa Cys Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
     50                  55                  60

Xaa Xaa Cys Xaa Pro Xaa Xaa Xaa Xaa Xaa Xaa Xaa Leu Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Cys Xaa Cys Xaa
            100

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Generic
      morphogenic sequence
<220> FEATURE:
```

```
<221> NAME/KEY: SITE
<222> LOCATION: (2)
<223> OTHER INFORMATION: Xaa=Lys, Arg, Gln, Ser, His, Glu, Ala, or Cys
<220> FEATURE:
<221> NAME/KEY: SITE
<222> LOCATION: (3)
<223> OTHER INFORMATION: Xaa=Lys, Arg, Met, Lys, Thr, Leu, Tyr, or Ala
<220> FEATURE:
<221> NAME/KEY: SITE
<222> LOCATION: (4)
<223> OTHER INFORMATION: Xaa=His, Gln, Arg, Lys, Thr, Leu, Val, Pro, or
      Tyr
<220> FEATURE:
<221> NAME/KEY: SITE
<222> LOCATION: (5)
<223> OTHER INFORMATION: Xaa=Gln, Thr, His, Arg, Pro, Ser. Ala, Tyr,
      Lys, Asp, or Leu

<400> SEQUENCE: 7

Cys Xaa Xaa Xaa Xaa
1               5

<210> SEQ ID NO 8
<211> LENGTH: 16
<212> TYPE: DNA
<213> ORGANISM: Artificial Sequence
<220> FEATURE:
<223> OTHER INFORMATION: Pax 6 consensus sequence
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 8
annttcacgc atgant                                                   16

<210> SEQ ID NO 9
<211> LENGTH: 11
<212> TYPE: DNA
<213> ORGANISM: Artificial Sequence
<220> FEATURE:
<223> OTHER INFORMATION: Pax 6 consensus sequence

<400> SEQUENCE: 9
ttcacgcatg a                                                        11

<210> SEQ ID NO 10
<211> LENGTH: 30
<212> TYPE: DNA
<213> ORGANISM: Homo sapiens

<400> SEQUENCE: 10
aagcttgatg cctgcacagt cagccctcag                                    30

<210> SEQ ID NO 11
<211> LENGTH: 30
<212> TYPE: DNA
<213> ORGANISM: Artificial Sequence
<220> FEATURE:
<223> OTHER INFORMATION: Reverse compliment primer

<400> SEQUENCE: 11
catcgcgccg gatccacgcg ctacccgggc                                    30

<210> SEQ ID NO 12
```

-continued

```
<211> LENGTH: 30
<212> TYPE: DNA
<213> ORGANISM: Homo sapiens

<400> SEQUENCE: 12
gcccgggtag cgcgtagagc cggcgcgatg                                  30

<210> SEQ ID NO 13
<211> LENGTH: 30
<212> TYPE: DNA
<213> ORGANISM: Artificial Sequence
<220> FEATURE:
<223> OTHER INFORMATION: Mutagenesis altered OP-1 sequence

<400> SEQUENCE: 13
gcccgggtag cgcgtggatc cggcgcgatg                                  30

<210> SEQ ID NO 14
<211> LENGTH: 57
<212> TYPE: DNA
<213> ORGANISM: Artificial Sequence
<220> FEATURE:
<223> OTHER INFORMATION: Altered OP-1 promoter in construct pAS3.3

<400> SEQUENCE: 14
gcccgggtag cgcgtggatc taagtaagct tggcattccg gtactgttgg taaaatg    57

<210> SEQ ID NO 15
<211> LENGTH: 10
<212> TYPE: DNA
<213> ORGANISM: Artificial Sequence
<220> FEATURE:
<223> OTHER INFORMATION: nucleic acid
<220> FEATURE:
<221> NAME/KEY: misc_feature
<222> LOCATION: (7)..(7)
<223> OTHER INFORMATION: N is g, a or t

<400> SEQUENCE: 15 tcacgcntga                                                        10
```